US010301359B2

(12) United States Patent
Sasisekharan et al.

(10) Patent No.: US 10,301,359 B2
(45) Date of Patent: May 28, 2019

(54) HUMAN ADAPTATION OF H3 INFLUENZA

(71) Applicant: Massachusetts Institute of Technology, Cambridge, MA (US)

(72) Inventors: Ram Sasisekharan, Lexington, MA (US); Kannan Tharakaraman, Arlington, MA (US); Rahul Raman, Waltham, MA (US)

(73) Assignee: MASSACHUSETTS INSTITUTE OF TECHNOLOGY, Cambridge, MA (US)

( * ) Notice: Subject to any disclaimer, the term of this patent is extended or adjusted under 35 U.S.C. 154(b) by 20 days.

(21) Appl. No.: 14/888,205

(22) PCT Filed: Apr. 30, 2014

(86) PCT No.: PCT/US2014/036174
§ 371 (c)(1),
(2) Date: Oct. 30, 2015

(87) PCT Pub. No.: WO2014/179464
PCT Pub. Date: Nov. 6, 2014

(65) Prior Publication Data

US 2016/0075742 A1 Mar. 17, 2016

Related U.S. Application Data

(60) Provisional application No. 61/817,479, filed on Apr. 30, 2013.

(51) Int. Cl.

| | |
|---|---|
| ***A61K 39/145*** | (2006.01) |
| ***A61K 39/12*** | (2006.01) |
| ***C12N 7/00*** | (2006.01) |
| ***C12N 7/01*** | (2006.01) |
| ***A61K 39/00*** | (2006.01) |
| ***C07K 14/005*** | (2006.01) |
| ***G01N 33/569*** | (2006.01) |
| ***C07K 16/10*** | (2006.01) |

(52) U.S. Cl.
CPC ............ *C07K 14/005* (2013.01); *A61K 39/12* (2013.01); *A61K 39/145* (2013.01); *C07K 16/1018* (2013.01); *C12N 7/00* (2013.01); *G01N 33/56983* (2013.01); *C12N 2760/16122* (2013.01); *C12N 2760/16134* (2013.01); *G01N 2333/11* (2013.01); *G01N 2469/10* (2013.01); *G01N 2469/20* (2013.01)

(58) Field of Classification Search
CPC ........ C07K 14/005; C12N 2760/16122; C12N 2760/16134; C12N 7/00; A61K 39/145
See application file for complete search history.

(56) References Cited

U.S. PATENT DOCUMENTS

| | | | | |
|---|---|---|---|---|
| 4,270,537 | A | 6/1981 | Romaine | |
| 4,596,556 | A | 6/1986 | Morrow et al. | |
| 4,790,824 | A | 12/1988 | Morrow et al. | |
| 4,886,499 | A | 12/1989 | Cirelli et al. | |
| 4,940,460 | A | 7/1990 | Casey, I. et al. | |
| 4,941,880 | A | 7/1990 | Burns | |
| 5,015,235 | A | 5/1991 | Crossman | |
| 5,064,413 | A | 11/1991 | McKinnon et al. | |
| 5,141,496 | A | 8/1992 | Dalto et al. | |
| 5,190,521 | A | 3/1993 | Hubbard et al. | |
| 5,312,335 | A | 5/1994 | McKinnon et al. | |
| 5,328,483 | A | 7/1994 | Jacoby | |
| 5,334,144 | A | 8/1994 | Alchas et al. | |
| 5,339,163 | A | 8/1994 | Homma et al. | |
| 5,383,851 | A | 1/1995 | McKinnon, Jr. et al. | |
| 5,417,662 | A | 5/1995 | Hjertman et al. | |
| 5,466,220 | A | 11/1995 | Brenneman | |
| 5,480,381 | A | 1/1996 | Weston | |
| 5,503,627 | A | 4/1996 | McKinnon et al. | |
| 5,520,639 | A | 5/1996 | Peterson et al. | |
| 5,527,288 | A | 6/1996 | Gross et al. | |
| 5,569,189 | A | 10/1996 | Parsons | |
| 5,599,302 | A | 2/1997 | Lilley et al. | |
| 5,649,912 | A | 7/1997 | Peterson | |
| 5,704,911 | A | 1/1998 | Parsons | |
| 5,893,397 | A | 4/1999 | Peterson et al. | |
| 5,993,412 | A | 11/1999 | Deily et al. | |
| 2007/0224205 | A1* | 9/2007 | Powell | A61K 39/0258 424/159.1 |

FOREIGN PATENT DOCUMENTS

| | | | |
|---|---|---|---|
| CA | 2766899 A1 | 1/2011 |
| WO | WO-1997/013537 A1 | 4/1997 |
| WO | WO-1997/037705 A1 | 10/1997 |
| WO | WO-1999/034850 A1 | 7/1999 |

(Continued)

OTHER PUBLICATIONS

NCBI GenBank Accession No. AAA43239.1; pdf p. 1.*
NCBI GenBank Accession No. AAA43239.1, 2006:pdf p. 1.*
Detmer, S.E. et al., Detection of Influenza A virus in porcine oral fluid samples, J. Vet. Diagn. Invest., 23(2):241-7 (2011).
International Search Report for PCT/US2014/036174, 3 pages (dated Sep. 19, 2014).
Written Opinion of PCT/US2014/036174, 10 pages (dated Sep. 19, 2014).
Allison, A.C., The mode of action of immunological adjuvants, Dev. Biol. Stand., 92:3-11 (1998).
Altschul, S. F. and Gish, W., Local Alignment Statistics, Methods in Enzymology, 266: 460-480 (1996).

(Continued)

*Primary Examiner* — Barry A Chestnut
(74) *Attorney, Agent, or Firm* — Choate, Hall & Stewart LLP; Brenda Herschbach Jarrell; Lisa A. Hawver

(57) ABSTRACT

The present invention provides, among other things, technologies and methodologies for detection, treatment, and/or prevention of influenza transmission and/or infection. The present invention also provides technologies for monitoring influenza variants for their potential to present a pandemic risk to humans.

6 Claims, 5 Drawing Sheets

Specification includes a Sequence Listing.

(56) References Cited

FOREIGN PATENT DOCUMENTS

WO WO2011003100 * 1/2011

OTHER PUBLICATIONS

Altschul, S. F. et al., Gapped BLAST and PSI-BLAST: a new generation of protein database search programs, Nucleic Acids Res., 25(17): 3389-3402 (1997).
Altschul, S.F. et al., Basic local alignment search tool, J. Mol. Biol., 215: 403-410 (1990).
Baylor, N.W. et al., Aluminum salts in vaccines—US perspective, Vaccine, 20:S18-23 (2002).
Cao, M. et al., Enhancement of the protective effect of inactivated influenza virus vaccine by cytokines, Vaccine, 10(4):238-242 (1992).
Connor, R. J. et al., Receptor specificity in human, avian, and equine H2 and H3 influenza virus isolates, Virology, 205:17-23 (1994).
Cooper, C. L. et al., Safety and immunogenicity of CPG 7909 injection as an adjuvant to Fluarix influenza vaccine, Vaccine, 22:3136-3143 (2004).
Cunha, B.A., Influenza: historical aspects of epidemics and pandemics, Infectious disease clinics of North America, 18: 141-155 (2004).
Eisen, M.B. et al., Binding of the influenza A virus to cell-surface receptors: structures of five hemagglutinin-sialyloligosaccharide complexes determined by X-ray crystallography, Virology, 232:19-31 (1997).
Gamblin, S.J. et al., The structure and receptor binding properties of the 1918 influenza hemagglutinin, Science, 303:1838-42 (2004).
Gaydos, J.C. et al., Swine influenza A outbreak, Fort Dix, New Jersey, 1976, Emerg. Infect. Dis., 12(1):23-28 (2006).
Ghochikyan, A. et al., Prototype Alzheimer's disease epitope vaccine induced strong Th2-type anti-Abeta antibody response with Alum to Quil A adjuvant switch, Vaccine, 24(13):2275-82 (2006).
Gupta, V. et al., Quantifying influenza vaccine efficacy and antigenic distance, Vaccine, 24(18):3881-3888 (2006).
Ha, Y. et al., X-ray structure of the hemagglutinin of a potential H3 avian progenitor of the 1968 Hong Kong pandemic influenza virus, Virology, 309:209-18 (2003).
Ha, Y. et al., X-ray structures of H5 avian and H9 swine influenza virus hemagglutinins bound to avian and human receptor analogs, Proc. Natl. Acad. Sci. USA, 98(20):11181-6 (2001).
Jayasena, S.D., Aptamers: an emerging class of molecules that rival antibodies in diagnostics, Clin. Chem., 45(9):1628-50 (1999).
Katz, J. M. et al., a nonionic block co-polymer adjuvant (CRL1005) enhances the immunogenicity and protective efficacy of inactivated influenza vaccine in young and aged mice, Vaccine, 18:2177-2187 (2000).
Kawaoka, Y. et al., Avian-to-human transmission of the PBI gene of influenza A viruses in the 1957 and 1968 pandemics, J Virol, 63(11):4603-4608 (1989).
Kreuter, J. and Liehl, E., Long-term studies of microencapsulated and adsorbed influenza vaccine nanoparticles, J. Pharm. Sci., 70(4):367-71 (1981).
Liu, J. et al., Structures of receptor complexes formed by hemagglutinins from the Asian Influenza pandemic of 1957, Proc. Natl. Acad. Sci. U S A, 106(40): 17175-80 (2009).
Mostow, S.R. et al., Application of the single radial diffusion test for assay of antibody to influenza type A viruses, J. Clin. Microbiol., 2(6):531-540 (1975).
Pappas, C. et al., Receptor Specificity and Transmission of H2N2 Subtype Viruses Isolated from the Pandemic of 1957, PLoS One, 5(6):e11158 (2010).
Phillips, N.C. and Emili, A. et al. Enhanced antibody response to liposome-associated protein antigens: preferential stimulation of IgG2a/b production, Vaccine, 10:151-158 (1992).
Rogers, G. N. and Paulson, J.C., Receptor determinants of human and animal influenza virus isolates: differences in receptor specificity of the H3 hemagglutinin based on species of origin, Virology, 127:361-73 (1983).
Rogers, G.N. et al., Single amino acid substitutions in influenza haemagglutinin change receptor binding specificity, Nature, 304:76-8 (1983).
Russell, R. J. et al., Avian and human receptor binding by hemagglutinins of influenza A viruses, Glycoconj. J., 23:85-92 (2006).
Sauter, N.K. et al., Binding of influenza virus hemagglutinin to analogs of its cell-surface receptor, sialic acid: analysis by proton nuclear magnetic resonance spectroscopy and X-ray crystallography, Biochemistry, 31(40):9609-21 (1992).
Schild, G.C. et al, a single-radial-immunodiffusion technique for the assay of influenza haemagglutinin antigen: Proposals for an assay method for the haemagglutinin content of influenza vaccines, Bull. World Health Organ., 52:223-31 (1975).
Schild, G.C. et al., Single-radial-haemolysis: a new method for the assay of antibody to influenza haemagglutinin, Bull. World Health Organ., 52:43-50 (1975).
Skehel, J.J. and Wiley, D.C., Receptor binding and membrane fusion in virus entry: the influenza hemagglutinin, Annu. Rev. Biochem., 69:531-569 (2000).
Srinivasan, A. et al., Quantitative biochemical rationale for differences in transmissibility of 1918 pandemic influenza A viruses, Proc. Natl. Acad. Sci. USA, 105(8):2800-2805 (2008).
Stevens, J. et al., Structure and receptor specificity of the hemagglutinin from an H5N1 influenza virus, Science, 312:404-10 (2006).
Stevens, J. et al., Structure of the uncleaved human H1 hemagglutinin from the extinct 1918 influenza virus, Science, 303:1866-70 (2004).
Tsuchiya, E. et al., Antigenic structure of the haemagglutinin of human influenza A/H2N2 virus, J. Gen Virol., 82:2475-2484 (2001).
Tuerk, C. and Gold, L., Systematic evolution of ligands by exponential enrichment: RNA ligands to bacteriophage T4 DNA polymerase, Science, 249:505-510 (1990).
Tumpey, T. M. et al., Characterization of the reconstructed 1918 Spanish influenza pandemic virus, Science, 310:77-80 (2005).
Tumpey, T.M. et al. A two-amino acid change in the hemagglutinin of the 1918 influenza virus abolishes transmission, Science, 315; 655-659 (2007).
Uiprasertkul, M. et al., Influenza A H5N1 replication sites in humans, Emerg. Infect. Dis. 11(7):1036-41 (2005).
Unkeless, J.C. et al. Structure and function of human and murine receptors for IgG, Annu. Rev. Immunol., 6:251-281 (1988).
Van Hoevan, N. et al. Human HA and polymerase subunit PB2 proteins confer transmission of an avian influenza virus through the air, PNAS, 106(9):3366-3371 (2009).
Viswanathan, K. et al., Determinants of glycan receptor specificity of H2N2 influenza A virus hemagglutinin, PLoS One, 5(10):e13768 (2010).
Webster, R.G. et al., Evolution and ecology of influenza A viruses, (Translated from eng) Microbiol Rev., 56(1):152-179 (1992).
Wentworth, D.E. et al., Transmission of swine influenza virus to humans after exposure to experimentally infected pigs, J. Infect Dis., 175:7-15 (1997).
Xu, R. et al., Structure, receptor binding, and antigenicity of influenza virus hemagglutinins from the 1957 H2N2 pandemic, J. Virol., 84(4): 1715-21 (2010).
Zhang, M. et al., Tracking global patterns of N-linked glycosylation site variation in highly variable viral glycoproteins: HIV, SIV, and HCV envelopes and influenza hemagglutinin, Glycobiology, 14(12):1229-1246 (2004).
Ge, S. and Wang, Z., An overview of influenza A virus receptors, Crit. Rev. Microbial., 37(2):157-65 (2011).
Igarashi, M. et al., Genetically destined potentials for N-linked glycosylation of influenza virus hemagglutinin, Virology, 376(2):323-329 (2008).
Mbawuike, I. N. et al., Enhancement of the protective efficacy of inactivated influenza A virus vaccine in aged mice by IL-2 liposomes, Vaccine, 8(4):347-352 (1990).
Nabel, G.J. et al., Vaccinate for the next H2N2 pandemic now, Nature, 471(7337):157-158 (2011).
Payne, L. G. et al., Poly[di(carboxylatophenoxy)phosphazene] (PCPP) is a potent immunoadjuvant for an influenza vaccine, Vaccine, 16:92-98 (1998).

(56) References Cited

OTHER PUBLICATIONS

Scholtissek C., et al., On the origin of the human influenza virus subtypes H2N2 and H3N2. (Translated from eng), Virology, 87(1):13-20 (1978).
Settembre, E.C. et al., H1N1: Can a pandemic cycle be broken?, Sci. Transl. Med., 2(24):24ps14 (2010).
Thompson, W.W. et al., Mortality associated with influenza and respiratory syncytial virus in the United States, JAMA, 289(2):179-186 (2003).
Wiley, D.C. et al., Structural identification of the antibody-binding sites of Hong Kong influenza haemagglutinin and their involvement in antigenic variation, Nature, 289(5796):373-378 (1981).
Wilson, I.A. et al., Structure of the haemagglutinin membrane glycoprotein of influenza virus at 3 A resolution, Nature, 289(5796):366-373 (1981).

* cited by examiner

SEQUENCE LISTING

<160> NUMBER OF SEQ ID NOS: 9

<210> SEQ ID NO 1
<211> LENGTH: 240
<212> TYPE: PRT
<213> ORGANISM: Influenza A virus

<400> SEQUENCE: 1

Lys Ile Cys Asn Asn Pro His Arg Ile Leu Asp Gly Ile Asp Cys Thr
1 5 10 15

Leu Ile Asp Ala Leu Leu Gly Asp Pro His Cys Asp Val Phe Gln Asn
20 25 30

Glu Thr Trp Asp Leu Phe Val Glu Arg Ser Lys Ala Phe Ser Asn Cys
35 40 45

Tyr Pro Tyr Asp Val Pro Asp Tyr Ala Ser Leu Arg Ser Leu Val Ala
50 55 60

Ser Ser Gly Thr Leu Glu Phe Ile Thr Glu Gly Phe Thr Trp Thr Gly
65 70 75 80

Val Thr Gln Asn Gly Gly Ser Asn Ala Cys Lys Arg Gly Pro Gly Ser
85 90 95

Gly Phe Phe Ser Arg Leu Asn Trp Leu Thr Lys Ser Gly Ser Thr Tyr
100 105 110

Pro Val Leu Asn Val Thr Met Pro Asn Asn Asp Asn Phe Asp Lys Leu
115 120 125

Tyr Ile Trp Gly Ile His His Pro Ser Thr Asn Gln Glu Gln Thr Ser
130 135 140

Leu Tyr Val Gln Ala Ser Gly Arg Val Thr Val Ser Thr Arg Arg Ser
145 150 155 160

Gln Gln Thr Ile Ile Pro Asn Ile Gly Ser Arg Pro Trp Val Arg Gly
165 170 175

Leu Ser Ser Arg Ile Ser Ile Tyr Trp Thr Ile Val Lys Pro Gly Asp
180 185 190

Val Leu Val Ile Asn Ser Asn Gly Asn Leu Ile Ala Pro Arg Gly Tyr
195 200 205

Phe Lys Met Arg Thr Gly Lys Ser Ser Ile Met Arg Ser Asp Ala Pro
210 215 220

Ile Asp Thr Cys Ile Ser Glu Cys Ile Thr Pro Asn Gly Ser Ile Pro
225 230 235 240

<210> SEQ ID NO 2
<211> LENGTH: 240
<212> TYPE: PRT
<213> ORGANISM: Influenza A virus

<400> SEQUENCE: 2

Glu Ile Cys Asn Asn Pro His Arg Val Leu Asp Gly Met Asp Cys Thr
1 5 10 15

Leu Ile Asp Ala Leu Leu Gly Asp Pro His Cys Asp Ser Leu Gln Asn
20 25 30

Glu Thr Trp Asp Leu Phe Ile Glu Arg Ser Glu Thr Ser Ser Asn Cys
35 40 45

Tyr Pro Tyr Asp Val Pro Gly Tyr Ala Ser Leu Arg Ser Ile Val Ala
50 55 60

Ser Ser Gly Thr Leu Glu Phe Ile Asn Glu Asp Phe Asn Trp Ala Gly
65 70 75 80

Val Thr Gln Asn Gly Gly Ser Ser Ala Cys Lys Arg Gly Ser Asp Asn

-continued

```
                85                  90                  95

Ser Phe Phe Ser Arg Leu Asn Trp Leu Tyr Lys Ser Gly Asn Thr Tyr
            100                 105                 110

Pro Met Leu Asn Val Thr Lys Pro Asn Asn Asp Asn Phe Asp Lys Leu
        115                 120                 125

Tyr Val Trp Gly Ile His His Pro Ser Thr Asn Gln Glu Gln Thr Arg
    130                 135                 140

Leu Tyr Ala Gln Glu Ser Gly Arg Ile Thr Val Ser Thr Lys Arg Ser
145                 150                 155                 160

Gln Gln Thr Val Thr Pro Asn Val Gly Pro Arg Pro Trp Ile Arg Gly
                165                 170                 175

Leu Ser Ser Arg Ile Ser Ile Tyr Trp Thr Ile Val Lys Ser Gly Asp
            180                 185                 190

Leu Leu Leu Ile Asn Ser Asn Gly Asn Leu Ile Ala Pro Arg Gly Tyr
        195                 200                 205

Phe Arg Leu Arg Ala Gly Lys Ser Ser Ile Ile Arg Ser Asp Ala Pro
    210                 215                 220

Ile Gly Thr Cys Ile Ser Glu Cys Ile Thr Pro Asn Gly Ser Ile Pro
225                 230                 235                 240


<210> SEQ ID NO 3
<211> LENGTH: 240
<212> TYPE: PRT
<213> ORGANISM: Influenza A virus

<400> SEQUENCE: 3

Glu Ile Cys Asn Asn Pro His Arg Val Leu Asp Gly Met Asp Cys Thr
1               5                   10                  15

Leu Ile Asp Ala Leu Leu Gly Asp Pro His Cys Asp Ser Leu Gln Asn
            20                  25                  30

Glu Thr Trp Asp Leu Phe Ile Glu Arg Ser Glu Ala Ser Ser Asn Cys
        35                  40                  45

Tyr Pro Tyr Asp Val Pro Gly Tyr Ala Ser Leu Arg Ser Ile Val Ala
    50                  55                  60

Ser Ser Gly Thr Leu Glu Phe Ile Asn Glu Asp Phe Asn Trp Ala Gly
65                  70                  75                  80

Val Thr Gln Asn Gly Gly Ser Ser Ala Cys Lys Arg Gly Ser Asp Asn
                85                  90                  95

Ser Phe Phe Ser Arg Leu Asn Trp Leu Tyr Lys Ser Gly Asn Thr Tyr
            100                 105                 110

Pro Met Leu Asn Val Thr Lys Pro Asn Asn Asp Asn Phe Asp Lys Leu
        115                 120                 125

Tyr Val Trp Gly Ile His His Pro Ser Thr Asn Gln Glu Gln Thr Arg
    130                 135                 140

Leu Tyr Ala Gln Glu Ser Gly Lys Ile Thr Val Ser Thr Lys Arg Asn
145                 150                 155                 160

Gln Gln Thr Val Thr Pro Asn Val Gly Pro Arg Pro Trp Val Arg Gly
                165                 170                 175

Leu Ser Ser Arg Ile Ser Ile Tyr Trp Thr Ile Val Lys Pro Gly Asp
            180                 185                 190

Leu Leu Leu Ile Asn Ser Asn Gly Asn Leu Ile Ala Pro Arg Gly Tyr
        195                 200                 205

Phe Arg Leu Arg Ala Gly Lys Ser Ser Ile Ile Arg Ser Asp Ala Pro
    210                 215                 220
```

Ile Gly Thr Cys Ile Ser Glu Cys Ile Thr Pro Asn Gly Ser Ile Pro
225 230 235 240

<210> SEQ ID NO 4
<211> LENGTH: 240
<212> TYPE: PRT
<213> ORGANISM: Influenza A virus

<400> SEQUENCE: 4

Glu Ile Cys Asn Asn Pro His Arg Val Leu Asp Gly Met Asp Cys Thr
1 5 10 15

Leu Ile Asp Ala Leu Leu Gly Asp Pro His Cys Asp Ser Leu Gln Asn
20 25 30

Glu Thr Trp Asp Leu Phe Val Glu Arg Ser Lys Ala Ser Ser Asn Cys
35 40 45

Tyr Pro Tyr Asp Val Pro Gly Tyr Ala Ser Leu Arg Ser Ile Val Ala
50 55 60

Ser Ser Gly Thr Leu Glu Phe Ile Asn Glu Asp Phe Asn Trp Ala Gly
65 70 75 80

Val Thr Gln Asn Gly Gly Ser Ser Ala Cys Lys Arg Gly Ser Asp Asn
85 90 95

Ser Phe Phe Ser Arg Leu Asn Trp Leu Tyr Lys Ser Gly Asn Thr Tyr
100 105 110

Pro Met Leu Asn Val Thr Lys Pro Asn Asn Asp Asn Phe Asp Lys Leu
115 120 125

Tyr Val Trp Gly Ile His His Pro Ser Thr Asn Gln Glu Gln Thr Arg
130 135 140

Leu Tyr Val Gln Glu Ser Gly Lys Ile Thr Val Ser Thr Lys Arg Asn
145 150 155 160

Gln Gln Thr Val Thr Pro Asn Val Gly Pro Arg Pro Trp Val Arg Gly
165 170 175

Leu Ser Ser Arg Ile Ser Ile Tyr Trp Thr Ile Val Lys Pro Gly Asp
180 185 190

Leu Leu Leu Ile Asn Ser Asn Gly Asn Leu Ile Ala Pro Arg Gly Tyr
195 200 205

Phe Arg Leu Arg Ala Gly Lys Ser Ser Ile Ile Arg Ser Asp Ala Pro
210 215 220

Ile Gly Thr Cys Ile Ser Glu Cys Ile Thr Pro Asn Gly Ser Ile Pro
225 230 235 240

<210> SEQ ID NO 5
<211> LENGTH: 240
<212> TYPE: PRT
<213> ORGANISM: Influenza A virus

<400> SEQUENCE: 5

Glu Ile Cys Asn Asn Pro His Arg Val Leu Asp Gly Met Asp Cys Thr
1 5 10 15

Leu Ile Asp Ala Leu Leu Gly Asp Pro His Cys Asp Ser Leu Gln Asn
20 25 30

Glu Thr Trp Asp Leu Phe Ile Glu Arg Ser Glu Ala Ser Ser Asn Cys
35 40 45

Tyr Pro Tyr Asp Val Pro Gly Tyr Ala Ser Leu Arg Ser Ile Val Ala
50 55 60

Ser Ser Gly Thr Leu Glu Phe Ile Asn Glu Asp Phe Asn Trp Ala Gly
65 70 75 80

```
Val Thr Gln Asn Gly Gly Ser Ser Ala Cys Lys Arg Gly Ser Asp Asn
                85                  90                  95

Ser Phe Phe Ser Arg Leu Asn Trp Leu Tyr Lys Ser Gly Asn Thr Tyr
            100                 105                 110

Pro Met Leu Asn Val Thr Lys Pro Asn Asn Asp Asn Phe Asp Lys Leu
        115                 120                 125

Tyr Val Trp Gly Ile His His Pro Ser Thr Asn Gln Glu Gln Thr Arg
    130                 135                 140

Leu Tyr Ala Gln Glu Ser Gly Lys Ile Thr Val Ser Thr Lys Arg Asn
145                 150                 155                 160

Gln Gln Thr Val Thr Pro Asn Val Gly Pro Arg Pro Trp Val Arg Gly
                165                 170                 175

Leu Ser Ser Arg Ile Ser Ile Tyr Trp Thr Ile Val Lys Pro Gly Asp
            180                 185                 190

Leu Leu Leu Ile Asn Ser Asn Gly Asn Leu Ile Ala Pro Arg Gly Tyr
        195                 200                 205

Phe Arg Leu Arg Ala Gly Lys Ser Ser Ile Ile Arg Ser Asp Ala Pro
    210                 215                 220

Ile Gly Thr Cys Ile Ser Glu Cys Ile Thr Pro Asn Gly Ser Ile Pro
225                 230                 235                 240


<210> SEQ ID NO 6
<211> LENGTH: 240
<212> TYPE: PRT
<213> ORGANISM: Influenza A virus

<400> SEQUENCE: 6

Glu Ile Cys Asn Asn Pro His Arg Val Leu Asp Gly Met Asp Cys Thr
1               5                   10                  15

Leu Ile Asp Ala Leu Leu Gly Asp Pro His Cys Asp Ser Leu Gln Asn
            20                  25                  30

Glu Thr Trp Asp Leu Phe Ile Glu Arg Ser Lys Ala Ser Ser Asn Cys
        35                  40                  45

Tyr Pro Tyr Asp Val Pro Gly Tyr Ala Ser Leu Arg Ser Ile Val Ala
    50                  55                  60

Ser Ser Gly Thr Leu Glu Phe Ile Asn Glu Asp Phe Asn Trp Ala Gly
65                  70                  75                  80

Val Thr Gln Asn Gly Gly Ser Ser Ala Cys Lys Arg Gly Ser Asp Asn
                85                  90                  95

Ser Phe Phe Ser Arg Leu Asn Trp Leu Tyr Lys Ser Gly Asn Thr Tyr
            100                 105                 110

Pro Met Leu Asn Val Thr Lys Pro Asn Asn Asp Asn Phe Asp Lys Leu
        115                 120                 125

Tyr Val Trp Gly Ile His His Pro Ser Thr Asn Gln Glu Gln Thr Arg
    130                 135                 140

Leu Tyr Ala Gln Glu Ser Gly Lys Ile Thr Val Ser Thr Lys Arg Asn
145                 150                 155                 160

Gln Gln Thr Val Thr Pro Asn Val Gly Pro Arg Pro Trp Val Arg Gly
                165                 170                 175

Leu Ser Ser Arg Ile Ser Ile Tyr Trp Thr Ile Val Lys Pro Gly Asp
            180                 185                 190

Leu Leu Leu Ile Asn Ser Asn Gly Asn Leu Ile Ala Pro Arg Gly Tyr
        195                 200                 205

Phe Arg Leu Arg Ala Gly Lys Ser Ser Ile Ile Arg Ser Asp Ala Pro
    210                 215                 220
```

Ile Gly Thr Cys Ile Ser Glu Cys Ile Thr Pro Asn Gly Ser Ile Pro
225 230 235 240

<210> SEQ ID NO 7
<211> LENGTH: 240
<212> TYPE: PRT
<213> ORGANISM: Influenza A virus

<400> SEQUENCE: 7

Glu Ile Cys Asn Asn Pro His Arg Val Leu Asp Gly Met Asp Cys Thr
1 5 10 15

Leu Ile Asp Ala Leu Leu Gly Asp Pro His Cys Asp Ser Leu Gln Asn
20 25 30

Glu Thr Trp Asp Leu Phe Ile Glu Arg Ser Glu Thr Ser Ser Asn Cys
35 40 45

Tyr Pro Tyr Asp Val Pro Gly Tyr Ala Ser Leu Arg Ser Ile Val Ala
50 55 60

Ser Ser Gly Thr Leu Glu Phe Ile Asn Glu Asp Phe Asn Trp Ala Gly
65 70 75 80

Val Thr Gln Asn Gly Gly Ser Ser Ala Cys Lys Arg Gly Ser Asp Asn
85 90 95

Ser Phe Phe Ser Arg Leu Asn Trp Leu Tyr Lys Ser Gly Asn Thr Tyr
100 105 110

Pro Met Leu Asn Val Thr Lys Pro Asn Asn Asp Asn Phe Asp Lys Leu
115 120 125

Tyr Val Trp Gly Ile His His Pro Ser Thr Asn Gln Glu Gln Thr Arg
130 135 140

Leu Tyr Ala Gln Glu Ser Gly Arg Ile Thr Val Ser Thr Lys Arg Ser
145 150 155 160

Gln Gln Thr Val Thr Pro Asn Val Gly Pro Arg Pro Trp Ile Arg Gly
165 170 175

Leu Ser Ser Arg Ile Ser Ile Tyr Trp Thr Ile Val Lys Ser Gly Asp
180 185 190

Leu Leu Leu Ile Asn Ser Asn Gly Asn Leu Ile Ala Pro Arg Gly Tyr
195 200 205

Phe Arg Leu Arg Ala Gly Lys Ser Ser Ile Ile Arg Ser Asp Ala Pro
210 215 220

Ile Gly Thr Cys Ile Ser Glu Cys Ile Thr Pro Asn Gly Ser Ile Pro
225 230 235 240

<210> SEQ ID NO 8
<211> LENGTH: 240
<212> TYPE: PRT
<213> ORGANISM: Influenza A virus

<400> SEQUENCE: 8

Glu Ile Cys Asp Ser Pro His Gln Ile Leu Asp Gly Glu Asn Cys Thr
1 5 10 15

Leu Ile Asp Ala Leu Leu Gly Asp Pro Gln Cys Asp Gly Phe Gln Asn
20 25 30

Lys Lys Trp Asp Leu Phe Val Glu Arg Ser Lys Ala Tyr Ser Asn Cys
35 40 45

Tyr Pro Tyr Asp Val Pro Asp Tyr Ala Ser Leu Arg Ser Leu Val Ala
50 55 60

Ser Ser Gly Thr Leu Glu Phe Asn Asn Glu Ser Phe Asn Trp Thr Gly
65 70 75 80

-continued

```
Val Thr Gln Asn Gly Thr Ser Ser Ala Cys Ile Arg Arg Ser Asn Asn
                85                  90                  95

Ser Phe Phe Ser Arg Leu Asn Trp Leu Thr His Leu Lys Phe Lys Tyr
            100                 105                 110

Pro Ala Leu Asn Val Thr Met Pro Asn Asn Glu Lys Phe Asp Lys Leu
        115                 120                 125

Tyr Ile Trp Gly Val His His Pro Gly Thr Asp Asn Asp Gln Ile Phe
    130                 135                 140

Pro Tyr Ala Gln Ala Ser Gly Arg Ile Thr Val Ser Thr Lys Arg Ser
145                 150                 155                 160

Gln Gln Thr Val Ile Pro Asn Ile Gly Ser Arg Pro Arg Val Arg Asn
                165                 170                 175

Ile Pro Ser Arg Ile Ser Ile Tyr Trp Thr Ile Val Lys Pro Gly Asp
            180                 185                 190

Ile Leu Leu Ile Asn Ser Thr Gly Asn Leu Ile Ala Pro Arg Gly Tyr
        195                 200                 205

Phe Lys Ile Arg Ser Gly Lys Ser Ser Ile Met Arg Ser Asp Ala Pro
    210                 215                 220

Ile Gly Lys Cys Asn Ser Glu Cys Ile Thr Pro Asn Gly Ser Ile Pro
225                 230                 235                 240


<210> SEQ ID NO 9
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 9

His His His His His His
1               5
```

HUMAN ADAPTATION OF H3 INFLUENZA

CROSS-REFERENCE TO RELATED APPLICATIONS

The present application claims priority to and benefit of U.S. Provisional Patent Application Ser. No. 61/817,479, filed Apr. 30, 2013, the entire contents of which are herein incorporated by reference.

GOVERNMENT SUPPORT

This invention was made with government support under Contract No. 6922267 awarded by the National Institutes of General Medical Sciences. The government has certain rights in the invention.

BACKGROUND

Influenza A viruses pose a major public health problem, causing seasonal epidemics and occasional—but devastating—global pandemics (Cunha B A (2004) Influenza: historical aspects of epidemics and pandemics. *Infectious disease clinics of North America* 18(1):141-155) which negatively impact the global economy. Until recently, influenza pandemics were thought to always be associated with the introduction of new HA subtypes into the human population. Indeed, two of the twentieth century pandemics—the 1957-58 H2N2 Asian Flu and the 1967-68 H3N2 Hong Kong Flu—involved precisely this scenario (Scholtissek C, Rohde W, Von Hoyningen V, & Rott R (1978) On the origin of the human influenza virus subtypes H2N2 and H3N2. (Translated from eng) *Virology* 87(1):13-20 and Kawaoka Y, Krauss S, & Webster R G (1989) Avian-to-human transmission of the PB1 gene of influenza A viruses in the 1957 and 1968 pandemics. (Translated from eng) *J Virol* 63(11):4603-4608).

However, more recent experiences have revealed that historical strains can sometimes re-emerge in the human population, with potentially devastating effects. This phenomenon results from influenza's mode of antigenic variation, and the interplay between the different host systems that impact it.

The surface glycoprotein HA of the influenza A virus is the main target of the immune system and mutations on the globular head region (residues 50-230 of HA1, H3 HA numbering used) of this protein determine antigenic novelty, species adaptation, and transmission (Webster R G, Bean W J, Gorman O T, Chambers T M, & Kawaoka Y (1992) Evolution and ecology of influenza A viruses. (Translated from eng) *Microbiol Rev* 56(1):152-179).

Birds are natural reservoirs for influenza A viruses and avian-adapted viruses regularly cross over to humans, either directly (through direct contact) or through an intermediate swine species. Influenza A virus strains rapidly evolve (through antigenic drift) in humans as a consequence of both the complex response of human immune system and rapid geographical movement of human population. In contrast to their rapid antigenic evolution in human hosts, the antigenic evolution of influenza A strains in avian and swine hosts occurs at a much slower rate. As a consequence of these factors, the human immunity to past pandemic strains fades over time, thus enabling antigenically "intact" viruses in avian and swine species to reemerge and begin a new infection cycle in humans.

For example, although H2N2 subtype does not currently circulate in the human population, virus strains with HAs that are antigenically similar to the 1957-58 pandemic H2N2 virus continue to circulate in avian species. Among the subtypes that continue to circulate in humans (H1N1 and H3N2), the 2009 H1N1 outbreak offers a practical example of how HA from a swine strain that is antigenically similar to 1918 pandemic H1N1 HA can be reintroduced into the human population. The question remains of whether this trend is observed in H3N2, given that there has been a high rate of antigenic drift in human H3 subtype since the emergence of 1968 pandemic H3N2.

The H3N2 pandemic began in 1968 and was caused by a human-adapted H2N2 virus that obtained avian H3 and PB1 genes through reassortment. The HAs of both 1957 and 1968 pandemic strains are of avian origin. Unlike H2N2, the H3N2 subtype is still in circulation, however the high rate of antigenic drift of human H3 coupled with the long interval since the previous pandemic may mean that the human herd would have 'forgotten' the antigenic structure of the 1968 pandemic strain and therefore the reemergence of a similar strain circulating in the avian or swine reservoir could have potentially damaging consequences. Identifying such strains is of paramount value for pandemic surveillance and preparedness; treating them is critical for survival.

SUMMARY

The present invention provides compositions and methods for use in the detection, treatment, and/or prevention of influenza transmission and/or infection. In some embodiments, the present invention provides vaccine compositions, diagnostic kits, methods of making vaccine compositions.

To address the question of whether a particular influenza strain presents a pandemic risk, some embodiments of the present invention measure the 'antigenic intactness' of HA from avian or swine species in reference to HA from corresponding pandemic subtypes. The "antigenic identity" (AI) of an avian or a swine HA is defined according to the present disclosure by the percentage fraction of amino acids in the immunodominant antigenic sites that are conserved in the corresponding pandemic HA (H1, H2 and H3 subtype). The AI value varies between 0 and 100. Values closer to 100 indicate a high antigenic identity with the pandemic HA.

In some embodiments, the present invention provides therapeutic agents, such as vaccine compositions, for treating or preventing influenza infection and/or transmission, particularly in humans. For example, the present disclosure describes engineered polypeptides whose amino acid sequence shows a high degree of sequence identity with a reference HA (e.g., a reference H3 HA), but differs in the presence of absence of certain defined sequence features. In general, the reference HA is one that does not mediate significant human infection and/or transmission (e.g. when tested in one or more established or described assay systems for assessing such human infection and/or transmission). In some embodiments, a provided engineered polypeptide is one that mediates human infection and/or transmission. In some embodiments, a provided engineered polypeptide shows human infection and/or transmission characteristics comparable to those of a reference HA that is known to mediate such human infection and/or transmission. The present invention provides such engineered HA polypeptides, and also provides fragments thereof, that are useful as or in therapeutic and/or prophylactic (e.g., vaccine) compositions.

The present invention also provides agents that detect provided polypeptides (e.g., engineered HA polypeptides and/or fragments thereof), for example, by direct or indirect binding thereto. In some embodiments, such detecting agents are or comprise antibodies that bind directly to one or more provided polypeptides. In some embodiments, detecting agents discriminate between a particular provided polypeptide and one or more reference HA polypeptides even when the provided polypeptide sequence differs from that of the reference HA polypeptide only in the presence or absence of one or more features set forth herein. In some embodiments, a binding agent distinguishes between a particular provided polypeptide and one or more reference HA polypeptides even when the provided polypeptide sequence differs from that of the reference HA only in the presence or absence of 1, 2, 3, 4, 5, or 6 such features.

In some embodiments, the present invention provides engineered polypeptides whose amino acid sequence includes an element corresponding to a reference sequence element, which reference sequence element comprises residues 53-278 of a reference H3 HA that does not mediate significant human infectivity, wherein the polypeptide's sequence element shows at least 80% overall sequence identity with the reference sequence element but is not identical to the reference sequence element in that it includes at least one of:

- i. a first antigenic site feature comprising
  - a. $Xaa_{122}$+$Xaa_{133}$+$Xaa_{137}$+$Xaa_{143}$+$Xaa_{144}$+$Xaa_{145}$+$Xaa_{146}$;
- ii. a second antigenic site feature comprising
  - a. $Xaa_{155}$+Ser186+$Xaa_{188}$+$Xaa_{189}$+$Xaa_{193}$;
- iii. a third antigenic site feature comprising
  - a. Asn53+$Xaa_{54}$+Asp275+$Xaa_{278}$;
- iv. a fourth antigenic site feature comprising
  - a. Arg201+Ser205+$Xaa_{207}$+Arg208+Ile217+Arg220;
- v. a fifth antigenic site feature comprising
  - a. $Xaa_{62}$+$Xaa_{78}$+$Xaa_{81}$+$Xaa_{83}$; and
- vi. at least one N-linked glycosylation feature at the amino acids corresponding to amino acids 81 and 165 of the reference H3HA, wherein the position of the amino acids of each feature corresponds to the referenced position of the reference H3 HA, and wherein $Xaa_{122}$ is either Thr or Gln, $Xaa_{133}$ is either Asn or Asp, $Xaa_{137}$ is selected from the group Asn, Gly, and Tyr, $Xaa_{143}$ is either Pro or Ser, $Xaa_{144}$ is selected from the group Gly, Ala, and Val, $Xaa_{145}$ is selected from the group Ser, Asn, and Lys, $Xaa_{146}$ is either Gly or Ser, $Xaa_{155}$ is either Thr or His, $Xaa_{188}$ is either Asn or Asp, $Xaa_{189}$ is either Gln or Arg, $Xaa_{193}$ is either Ser or Asn, $Xaa_{54}$ is either Asn or Ser, $Xaa_{278}$ is either Ile or Asn, $Xaa_{207}$ is either Arg or Lys, $Xaa_{62}$ is selected from the group Ile, Arg, and Lys, $Xaa_{78}$ is either Val or Asp, $Xaa_{81}$ is either Asn or Asp, and $Xaa_{83}$ is either Thr or Lys.

In some embodiments, provided polypeptides have a length between a lower bound of about 100 amino acids and an upper bound of about 400 amino acids, inclusive. In some embodiments, the lower bound is about 200 amino acids and the upper bound is about 300 amino acids, inclusive.

In some embodiments, the invention provides techniques and reagents for detecting, characterizing, and/or monitoring influenza infection or risk thereof. In some embodiments, provided techniques and/or reagents are utilized to detect, characterize and/or monitor influenza strains present in a single individual organism, (e.g., in a single human being). In some embodiments, provided techniques and/or reagents are utilized to detect, characterize, and/or monitor influenza strains present in a population of organisms (e.g., of human beings). In some embodiments, provided techniques and/or reagents are utilized to detect, characterize, and/or monitor influenza strains present in an area or environment (e.g., such as from an environmental source). In some embodiments, provided techniques and/or reagents are used to periodically monitor at least one or an organism, a population of organisms, and an area or environment. In some embodiments, the period between measurement is between one hour and one year, inclusive. In some embodiments, the period of time between measurement is between one day and six months, inclusive.

DEFINITIONS

Figure 1:
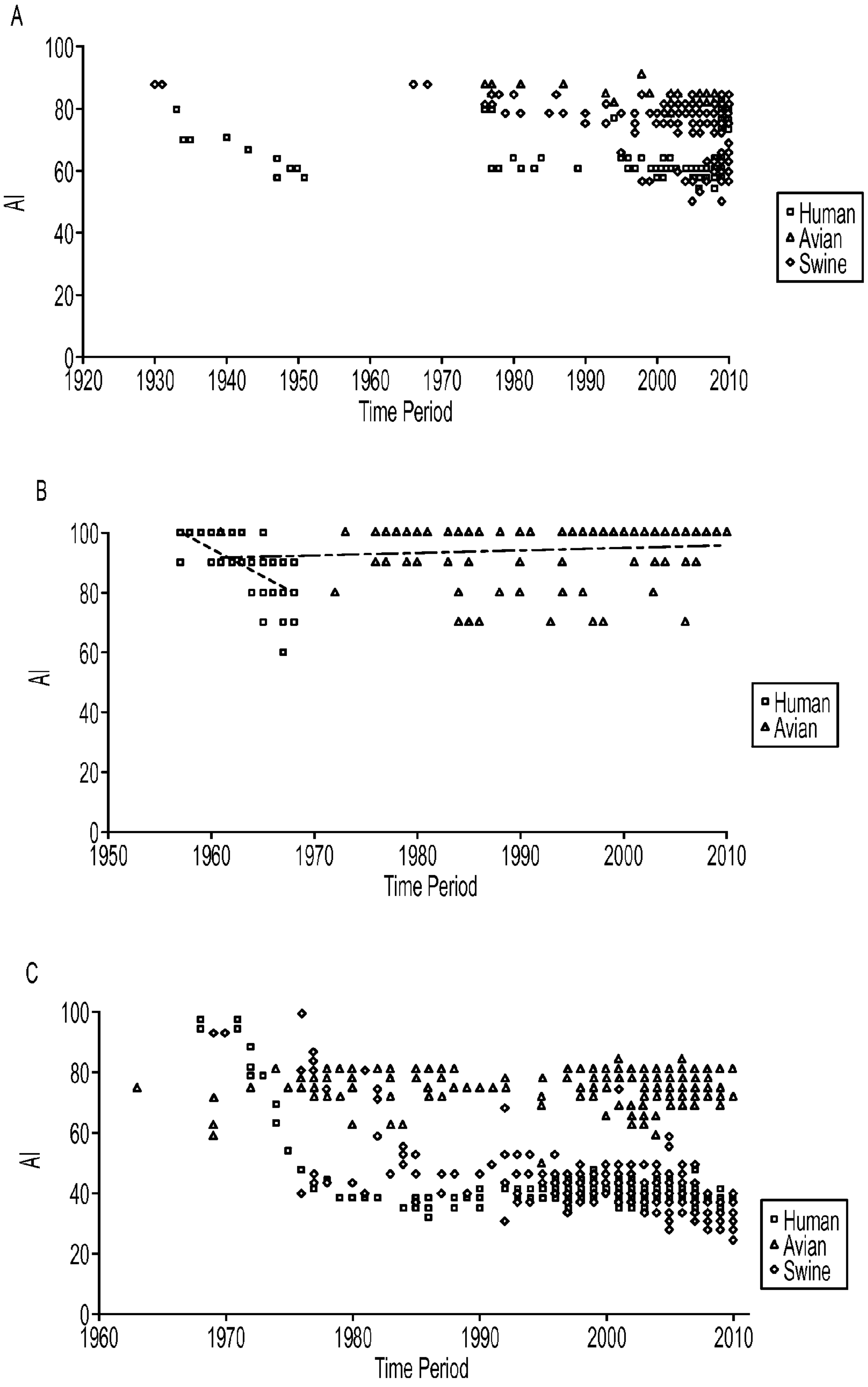
FIG. 1 shows antigenic identity from exemplary human, avian and swine species relative to pandemics of note, specifically A. 1918-19 H1N1, B. 1957-58 H2N2, and C. 1968-69 H3N2 each plotted against the year of isolation.

Affinity: As is known in the art, "affinity" is a measure of the tightness with a particular ligand (e.g., an HA polypeptide) binds to its partner (e.g., an HA receptor, one or more glycans, etc). Affinities can be measured in different ways. In some embodiments, affinity is measured by a quantitative assay (e.g., glycan binding assays). In some such embodiments, binding partner concentration (e.g., HA receptor, glycan, etc.) may be fixed to be in excess of ligand (e.g., an HA polypeptide) concentration so as to mimic physiological conditions (e.g., viral HA binding to cell surface glycans). In some embodiments, binding partner concentration may be fixed to so that ligand is in excess. Alternatively or additionally, in some embodiments, binding partner (e.g., HA receptor, glycan, etc.) concentration and/or ligand (e.g., an HA polypeptide) concentration may be varied. In some embodiments, affinity is assessed over a range of concentrations (e.g., serial dilutions) of ligand and/or of binding partner. In some embodiments, affinity (e.g., binding affinity) may be compared to a reference (e.g., a wild type HA that mediates infection of a humans) under comparable conditions (e.g., concentrations).

Antibody: As used herein, the term "antibody" refers to a polypeptide that includes canonical immunoglobulin sequence elements sufficient to confer specific binding to a particular target antigen. As is known in the art, intact antibodies as produced in nature are approximately 150 kD tetrameric agents comprised of two identical heavy chain polypeptides (about 50 kD each) and two identical light chain polypeptides (about 25 kD each) that associate with each other into what is commonly referred to as a "Y-shaped" structure. Each heavy chain is comprised of at least four domains (each about 110 amino acids long)—an amino-terminal variable (VH) domain (located at the tips of the Y structure), followed by three constant domains: CH1, CH2, and the carboxy-terminal CH3 (located at the base of the Y's stem). A short region, known as the "switch", connects the heavy chain variable and constant regions. The "hinge" connects CH2 and CH3 domains to the rest of the antibody. Two disulfide bonds in this hinge region connect the two heavy chain polypeptides to one another in an intact antibody. Each light chain is comprised of two domains—an amino-terminal variable (VL) domain, followed by a carboxy-terminal constant (CL) domain, separated from one another by another "switch". Intact antibody tetramers are comprised of two heavy chain-light chain dimers in which the heavy and light chains are linked to one another by a single disulfide bond; two other disulfide bonds connect the heavy chain hinge regions to one another, so that the dimers are connected to one another and the tetramer is formed. Naturally-produced antibodies are also glycosylated, typically on the CH2 domain. Each domain in a natural antibody has a structure characterized by an "immunoglobulin fold" formed from two beta sheets (e.g., 3-, 4-, or 5-stranded sheets) packed against each other in a compressed antiparallel beta barrel. Each variable domain contains three hypervariable loops known as "complement determining regions" (CDR1, CDR2, and CDR3) and four somewhat invariant "framework" regions (FR1, FR2, FR3, and FR4). When natural antibodies fold, the FR regions form the beta sheets that provide the structural framework for the domains, and the CDR loop regions from both the heavy and light chains are brought together in three-dimensional space so that they create a single hypervariable antigen binding site located at the tip of the Y structure. Amino acid sequence comparisons among antibody polypeptide chains have defined two light chain (κ and λ) classes, several heavy chain (e.g., μ, γ, α, ε, δ) classes, and certain heavy chain subclasses (α1, α2, γ1, γ2, γ3, and γ4). Antibody classes (IgA [including IgA1, IgA2], IgD, IgE, IgG [including IgG1, IgG2, IgG3, IgG4], IgM) are defined based on the class of the utilized heavy chain sequences. For purposes of the present invention, in certain embodiments, any polypeptide or complex of polypeptides that includes sufficient immunoglobulin domain sequences as found in natural antibodies can be referred to and/or used as an "antibody", whether such polypeptide is naturally produced (e.g., generated by an organism reacting to an antigen), or produced by recombinant engineering, chemical synthesis, or other artificial system or methodology. In some embodiments, an antibody is monoclonal; in some embodiments, an antibody is monoclonal. In some embodiments, an antibody has constant region sequences that are characteristic of mouse, rabbit, primate, or human antibodies. In some embodiments, an antibody sequence elements are humanized, primatized, chimeric, etc, as is known in the art. Moreover, the term "antibody" as used herein, will be understood to encompass (unless otherwise stated or clear from context) can refer in appropriate embodiments to any of the art-known or developed constructs or formats for capturing antibody structural and functional features in alternative presentation. For example, in some embodiments, the term can refer to bi- or other multi-specific (e.g., zybodies, etc) antibodies, Small Modular ImmunoPharmaceuticals ("SMIPs™"), single chain antibodies, cameloid antibodies, and/or antibody fragments. In some embodiments, an antibody may lack a covalent modification (e.g., attachment of a glycan) that it would have if produced naturally. In some embodiments, an antibody may contain a covalent modification (e.g., attachment of a glycan, a payload [e.g., a detectable moiety, a therapeutic moiety, a catalytic moiety, etc], or other pendant group [e.g., poly-ethylene glycol, etc]

Antibody fragment: As used herein, an "antibody fragment" includes a portion of an intact antibody, such as, for example, the antigen-binding or variable region of an antibody. Examples of antibody fragments include Fab, Fab', F(ab')2, and Fv fragments; triabodies; tetrabodies; linear antibodies; single-chain antibody molecules; and CDR-containing moieties included in multi-specific antibodies formed from antibody fragments. Those skilled in the art will appreciate that the term "antibody fragment" does not imply and is not restricted to any particular mode of generation. An antibody fragment may be produced through use of any appropriate methodology, including but not limited to cleavage of an intact antibody, chemical synthesis, recombinant production, etc.

Antigen: The term "antigen", as used herein, refers to an agent that elicits an immune response; and/or (ii) an agent that is bound by a T cell receptor (e.g., when presented by an MHC molecule) or to an antibody (e.g., produced by a B cell) when exposed or administered to an organism. In some embodiments, an antigen elicits a humoral response (e.g., including production of antigen-specific antibodies) in an organism; alternatively or additionally, in some embodiments, an antigen elicits a cellular response (e.g., involving T-cells whose receptors specifically interact with the antigen) in an organism. It will be appreciated by those skilled in the art that a particular antigen may elicit an immune response in one or several members of a target organism (e.g., mice, rabbits, primates, humans), but not in all members of the target organism species. In some embodiments, an antigen elicits an immune response in at least about 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99% of the members of a target organism species. In some embodiments, an antigen binds to an antibody and/or T cell receptor, and may or may not induce a particular physiological response in an organism. In some embodiments, for example, an antigen may bind to an antibody and/or to a T cell receptor in vitro, whether or not such an interaction occurs in vivo. In general, an antigen may be or include any chemical entity such as, for example, a small molecule, a nucleic acid, a polypeptide, a carbohydrate, a lipid, a polymer (in some embodiments other than a biologic polymer [e.g., other than a nucleic acid or amino acid polymer) etc. In some embodiments, an antigen is or comprises a polypeptide. In some embodiments, an antigen is or comprises a glycan. Those of ordinary skill in the art will appreciate that, in general, an antigen may be provided in isolated or pure form, or alternatively may be provided in crude form (e.g., together with other materials, for example in an extract such as a cellular extract or other relatively crude preparation of an antigen-containing source). In some embodiments, antigens utilized in accordance with the present invention are provided in a crude form. In some embodiments, an antigen is or comprises a recombinant antigen.

Antigenic Identity: as used herein, the term "antigenic identity" (AI) refers to the percentage fraction of amino acids in a polypeptide of interest, or portion thereof (e.g in. an HA polypeptide, or in an epitope [e.g., an immunodominant epitope] thereof), that are shared with a relevant reference polypeptide (e.g., a parent HA polypeptide that may, for example, be a pandemic HA), or portion thereof. The AI value resulting from comparison of any two polypeptides or sequences can be a number between 0 and 100, with a value of 100 indicating the two polypeptides, or portions thereof, are identical in sequence.

Approximately: As used herein, the term "approximately" or "about," as applied to one or more values of interest, refers to a value that is similar to a stated reference value. In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

Aptamer: As used herein, the term "aptamer" means a macromolecule composed of nucleic acid (e.g., RNA, DNA) that binds tightly to a specific molecular target (e.g., an umbrella topology glycan). A particular aptamer may be described by a linear nucleotide sequence and is typically about 15-60 nucleotides in length. Without wishing to be bound by any theory, it is contemplated that the chain of nucleotides in an aptamer form intramolecular interactions that fold the molecule into a complex three-dimensional shape, and this three-dimensional shape allows the aptamer to bind tightly to the surface of its target molecule. Given the extraordinary diversity of molecular shapes that exist within the universe of all possible nucleotide sequences, aptamers may be obtained for a wide array of molecular targets, including proteins and small molecules. In addition to high specificity, aptamers have very high affinities for their targets (e.g., affinities in the picomolar to low nanomolar range for proteins). Aptamers are chemically stable and can be boiled or frozen without loss of activity. Because they are synthetic molecules, they are amenable to a variety of modifications, which can optimize their function for particular applications. For example, aptamers can be modified to dramatically reduce their sensitivity to degradation by enzymes in the blood for use in in vivo applications. In addition, aptamers can be modified to alter their biodistribution or plasma residence time.

Associated with: Two events or entities are "associated" with one another, as that term is used herein, if the presence, level and/or form of one is correlated with that of the other. For example, a particular entity (e.g., polypeptide) is considered to be associated with a particular disease, disorder, or condition, if its presence, level and/or form correlates with incidence of and/or susceptibility of the disease, disorder, or condition (e.g., across a relevant population). In some embodiments, two or more entities are physically "associated" with one another if they interact, directly or indirectly, so that they are and remain in physical proximity with one another. In some embodiments, two or more entities that are physically associated with one another are covalently linked to one another; in some embodiments, two or more entities that are physically associated with one another are not covalently linked to one another but are non-covalently associated, for example by means of hydrogen bonds, van der Waals interaction, hydrophobic interactions, magnetism, and combinations thereof. Binding: It will be understood that the term "binding", as used herein, typically refers to a non-covalent association between or among two or more entities. "Direct" binding involves physical contact between entities or moieties; indirect binding involves physical interaction by way of physical contact with one or more intermediate entities. Binding between two or more entities can be assessed in any of a variety of contexts—including where interacting entities or moieties are studied in isolation or in the context of more complex systems (e.g., while covalently or otherwise associated with a carrier entity and/or in a biological system or cell).

Biologically active: As used herein, the phrase "biologically active" refers to a characteristic of any agent that has activity in a biological system, and particularly in an organism. For instance, an agent that, when administered to an organism, has a biological effect on that organism, is considered to be biologically active. In particular embodiments, where a protein or polypeptide is biologically active, a portion of that protein or polypeptide that shares at least one biological activity of the protein or polypeptide is typically referred to as a "biologically active" portion.

Characteristic Portion: As used herein, the term "characteristic portion" is used, in the broadest sense, to refer to a portion of a substance whose presence (or absence) correlates with presence (or absence) of a particular feature, attribute, or activity of the substance. In some embodiments, a characteristic portion of a substance is a portion that is found in the substance and in related substances that share the particular feature, attribute or activity, but not in those that do not share the particular feature, attribute or activity.

Characteristic Pandemic Feature: As used herein the term "characteristic pandemic feature" is one that is found in at least one reference pandemic strain and not in at least one non-pandemic strain. In some embodiments, a characteristic pandemic feature is one that is commonly found in pandemic strains and rarely found in non-pandemic strains. In some embodiments, a characteristic pandemic feature shows prevalence among representative pandemic strains that is at least 130% of that observed among representative non-pandemic strains. In some embodiments, a characteristic pandemic feature shows prevalence among representative pandemic strains that is at least 150%, 200%, 300%, 500% or 1,000% of that observed among representative non-pandemic strains Characteristic sequence element: As used herein, the phrase "characteristic sequence element" refers to a sequence element found in a polymer (e.g., in a polypeptide or nucleic acid) that represents a characteristic portion of that polymer. In some embodiments, presence of a characteristic sequence element correlates with presence or level of a particular activity or property of the polymer. In some embodiments, presence (or absence) of a characteristic sequence element defines a particular polymer as a member (or not a member) of a particular family or group of such polymers. A characteristic sequence element typically comprises at least two monomers (e.g., amino acids or nucleotides). In some embodiments, a characteristic sequence element includes at least 2, 3, 4, 5, 6, 7, 8, 9, 10, 11, 12, 13, 14, 15, 20, 25, 30, 35, 40, 45, 50, or more monomers (e.g., contiguously linked monomers). In some embodiments, a characteristic sequence element includes at least first and second stretches of continuous monomers spaced apart by one or more spacer regions whose length may or may not vary across polymers that share the sequence element.

Combination therapy: The term "combination therapy", as used herein, refers to those situations in which two or more different pharmaceutical agents are administered in overlapping regimens so that the subject is simultaneously exposed to both agents. In some embodiments, the two or more pharmaceutical agents are administered simultaneously. In some embodiments, the two or more pharmaceutical agents are administered sequentially.

Comparable: The term "comparable", as used herein, refers to two or more agents, entities, situations, sets of conditions, etc that may not be identical to one another but that are sufficiently similar to permit comparison therebetween so that conclusions may reasonably be drawn based on differences or similarities observed. Those of ordinary skill in the art will understand, in context, what degree of identity is required in any given circumstance for two or more such agents, entities, situations, sets of conditions, etc to be considered comparable.

Corresponding to: As used herein, the term "corresponding to" is often used to designate the position/identity of an amino acid residue in a polypeptide of interest (e.g., an HA polypeptide). Those of ordinary skill will appreciate that, for purposes of simplicity, residues in a polypeptide are often designated using a canonical numbering system based on a reference related polypeptide, so that an amino acid "corresponding to" a residue at position 190, for example, need not actually be the $190^{th}$ amino acid in a particular amino acid chain but rather corresponds to the residue found at 190 in the reference polypeptide; those of ordinary skill in the art readily appreciate how to identify "corresponding" amino acids. Typically, residues in HA polypeptides are designated with reference to a canonical wild type H3 HA, and reference in a polypeptide of interest that correspond to resides in the canonical wild type H3 HA are described using the numbering of the residues to which they correspond.

Determine: Many methodologies described herein include a step of "determining". Those of ordinary skill in the art, reading the present specification, will appreciate that such "determining" can utilize any of a variety of techniques available to those skilled in the art, including for example specific techniques explicitly referred to herein. In some embodiments, a determination involves manipulation of a physical sample. In some embodiments, a determination involves consideration and/or manipulation of data or information, for example utilizing a computer or other processing unit adapted to perform a relevant analysis. In some embodiments, a determination involves receiving relevant information and/or materials from a source. In some embodiments, determining involves comparing one or more features of a sample or entity to a comparable reference.

Direct-binding amino acids: As used herein, the phrase "direct-binding amino acids" refers to HA polypeptide amino acids which interact directly with one or more glycans that is/are associated with host cell HA receptors.

Dosage form: The term "dosage form" is used herein to refer to a physically discrete unit of a therapeutic composition to be administered to a patient. A "unit dosage form" contains an amount of active agent(s) equivalent to a single dose, although it is understood that a prescribing physician may instruct multiple unit dosage forms, or partial unit dosage forms, be administered as a single dose.

Dosing regimen: A "dosing regimen" (or "therapeutic regimen"), as that term is used herein, is a set of unit doses (typically more than one) that are administered individually to a subject, typically separated by periods of time. In some embodiments, a given therapeutic agent has a recommended dosing regimen, which may involve one or more doses. In some embodiments, a dosing regimen comprises a plurality of doses each of which are separated from one another by a time period of the same length; in some embodiments, a dosing regimen comprises a plurality of doses and at least two different time periods separating individual doses. In some embodiments, a dosing regimen is correlated with a particular outcome, event, or probability of such.

Engineered: The term "engineered", as used herein, describes a polypeptide whose amino acid sequence has been selected by man and/or whose production required action of the hand of man. For example, an engineered HA polypeptide has an amino acid sequence that differs from the amino acid sequences of HA polypeptides found in natural influenza isolates. In some embodiments, an engineered HA polypeptide has an amino acid sequence that differs from the amino acid sequence of HA polypeptides included in the NCBI database.

Expression: The term "expression", when used in reference to a nucleic acid herein, refers to one or more of the following events: (1) production of an RNA transcript of a DNA template (e.g., by transcription); (2) processing of an RNA transcript (e.g., by splicing, editing, 5' cap formation, and/or 3' end formation); (3) translation of an RNA into a polypeptide; and/or (4) post-translational modification of a polypeptide.

Fold: The term "fold" is used herein in accordance with its art understood meaning referring to a structural element of a polypeptide that has adopted or can adopt a three-dimensional structure. For example, a fold may be or comprise one or more helices (e.g., alpha-helices) and/or one or more sheets (e.g., beta-sheets).

Foldome: As used herein, the term "foldome" refers to the set of polypeptide folds encoded by an organism genome. As will be appreciated by those skilled in the art, in some embodiments, the foldome includes all encoded polypeptide folds; in some embodiments, the foldome includes polypeptide folds present in expressed polypeptides (e.g., in all expressed polypeptides or in polypeptides expressed only under certain conditions such as in certain tissues, at certain times in development, etc.).

Hemagglutinin (HA) polypeptide: As used herein, the term "hemagglutinin polypeptide" (or "HA polypeptide') refers to a polypeptide whose amino acid sequence includes at least one characteristic sequence of HA. A wide variety of HA sequences from influenza isolates are known in the art; indeed, the National Center for Biotechnology Information (NCBI) maintains a database (ncbi.nlm.nih.gov/genomes/FLU/) that, as of the filing of the present application included at least 9796 HA sequences. Those of ordinary skill in the art, referring to this database, can readily identify sequences that are characteristic of HA polypeptides generally, and/or of particular HA polypeptides (e.g., H1, H2, H3, H4, H5, H6, H7, H8, H9, H10, H11, H12, H13, H14, H15, or H16 polypeptides; or of HAs that mediate infection of particular hosts, e.g., avian, camel, canine, cat, civet, environment, equine, human, leopard, mink, mouse, seal, stone martin, swine, tiger, whale, etc. For example, in some embodiments, an HA polypeptide includes one or more characteristic sequence elements found between about residues 97 and about 185, about 324 and about 340, about 96 and about 100, and/or about 130 and about 230 of an HA protein found in a natural isolate of an influenza virus. In some embodiments, an HA polypeptide has an amino acid sequence comprising at least one of HA Sequence Elements 1 and 2, as defined herein.

H3 HA polypeptide: An "H3 HA polypeptide", as that term is used herein, is an HA polypeptide whose amino acid sequence includes at least one sequence element that is characteristic of H3 and distinguishes H3 from other HA subtypes. Representative such sequence elements can be determined by alignments as will be understood by those skilled in the art.

High Affinity Binding: The term "high affinity binding", as used herein refers to a high degree of tightness with which a particular ligand (e.g., an HA polypeptide) binds to its partner (e.g., an HA receptor). Affinities can be measured by any available method, including those known in the art. In some embodiments, binding is considered to be high affinity if the Kd' is about 500 pM or less (e.g., below about 400 pM, about 300 pM, about 200 pM, about 100 pM, about 90 pM, about 80 pM, about 70 pM, about 60 pM, about 50 pM, about 40 pM, about 30 pM, about 20 pM, about 10 pM, about 5 pM, about 4 pM, about 3 pM, about 2 pM, etc.) in binding assays. In some embodiments, binding is considered to be high affinity if the affinity is stronger (e.g., the Kd' is lower) for a polypeptide of interest than for a selected reference polypeptide. In some embodiments, binding is considered to be high affinity if the ratio of the Kd' for a polypeptide of interest to the Kd' for a selected reference polypeptide is 1:1 or less (e.g., 0.9:1, 0.8:1, 0.7:1, 0.6:1, 0.5:1. 0.4:1, 0.3:1, 0.2:1, 0.1:1, 0.05:1, 0.01:1, or less). In some embodiments, binding is considered to be high affinity if the Kd' for a polypeptide of interest is about 100% or less (e.g., about 99%, about 98%, about 97%, about 96%, about 95%, about 90%, about 85%, about 80%, about 75%, about 70%, about 65%, about 60%, about 55%, about 50%, about 45%, about 40%, about 35%, about 30%, about 25%, about 20%, about 15%, about 10%, about 5%, about 4%, about 3%, about 2%, about 1% or less) of the Kd' for a selected reference polypeptide.

Host: The term "host" is used herein to refer to a system (e.g., a cell, organism, etc) in which a polypeptide of interest is present. In some embodiments, a host is a system that is susceptible to infection with a particular infectious agent. In some embodiments, a host is a system that expresses a particular polypeptide of interest.

IgE binding site: An "IgE binding site" is a region of an antigen that is recognized by an anti-antigen IgE molecule. Such a region is necessary and/or sufficient to result in (i) binding of the antigen to IgE; (ii) cross-linking of anti-antigen IgE; (iii) degranulation of mast cells containing surface-bound anti-antigen IgE; and/or (iv) development of allergic symptoms (e.g., histamine release). In general, IgE binding sites are defined for a particular antigen or antigen fragment by exposing that antigen or fragment to serum from allergic individuals (preferably of the species to whom inventive compositions are to be administered). It will be recognized that different individuals may generate IgE that recognize different epitopes on the same antigen. Thus, it is typically desirable to expose antigen or fragment to a representative pool of serum samples. For example, where it is desired that sites recognized by human IgE be identified in a given antigen or fragment, serum is preferably pooled from at least 5-10, preferably at least 15, individuals with demonstrated allergy to the antigen. Those of ordinary skill in the art will be well aware of useful pooling strategy in other contexts.

Immunodominant: A particular epitope is considered to be "immunodominant" if it (i) is responsible for a significant fraction of the IgE binding observed with the intact antigen; and/or (ii) is recognized by IgE in a significant fraction of sensitive individuals. An immunodominant epitope is often defined in reference to the other observed epitopes. For example, all IgE epitopes in a given antigen can be assayed simultaneously (e.g., by immunoblot) and the immunodominant epitopes can be identified by their strength as compared with the other epitopes. Usually, but not always, an immunodominant epitope will contribute at least 10% of the binding reactivity observed in such a study. Alternatively or additionally, an epitope can be classified as immunodominant if it is recognized by IgE in sera of a significant fraction, preferably at least a majority, more preferably at least about 60%, 70%, 80%, 90%, 95%, 99%, or 100%, of sensitive individuals.

Infectious agent: An "infectious agent" is one that infects at least one host. In some embodiments, an infectious agent is or comprises a viral agent (e.g., a DNA or RNA-based virus). Those of ordinary skill in the art are well familiar with a variety of infectious agents and/or their classification. To give but a few examples, in some embodiments an infectious agent is or comprises a viral agent selected from the group consisting of influenza virus, Human Immunodeficiency virus (HIV), Varicella zoster, rhinovirus, coronavirus, Dengue virus, ebola virus, enterovirus, parvovirus, herpes, hepatitis A, hepatitis B, hepatitis C, hepatitis D, hepatitis E, papillomavirus, epstein ban, measles, mumps, polio, rabies, respiratory syncytial virus, rotavirus, rubella, west nile, yellow fever, and combinations thereof.

Infectious disease polypeptide: As used herein, the term "infectious disease polypeptide" refers to a polypeptide that is naturally produced by an infectious agent, involved in mediating infection, and/or otherwise associated with infection. In some embodiments, an infectious disease polypeptide is one to which a host organism raises an immune response upon infection. In some embodiments, such an immune response comprises an antibody response (e.g., that includes generating and/or amplifying antibodies specific for the infectious disease polypeptide). In some embodiments, such an immune response comprises a T-cell response (e.g., that includes generating T-cells whose receptors recognize infectious disease polypeptides). In some embodiments, an infectious disease polypeptide is one that is produced by (e.g., encoded by the genome of) an infectious agent. In some embodiments, an infectious disease polypeptide is produced by (e.g., is encoded by the genome of) a host cell or organism that is susceptible to infection by an infectious agent.

Isolated: The term "isolated", as used herein, refers to an agent or entity that has either (i) been separated from at least some of the components with which it was associated when initially produced (whether in nature or in an experimental setting); or (ii) produced by the hand of man. Isolated agents or entities may be separated from at least about 10%, at least about 20%, at least about 30%, at least about 40%, at least about 50%, at least about 60%, at least about 70%, at least about 80%, at least about 90%, or more of the other components with which they were initially associated. In some embodiments, isolated agents are more than 90%, 91%, 92%, 93%, 94%, 95%, 96%, 97%, 98%, 99% pure.

Low affinity binding: The term "low affinity binding", as used herein refers to a low degree of tightness with which a particular ligand (e.g., an HA polypeptide) binds to its partner (e.g., an HA receptor). As described herein, affinities can be measured by any available method, including methods known in the art. In some embodiments, binding is considered to be low affinity if the Kd' is about 100 pM or more (e.g., above about 200 pM, 300 pM, 400 pM, 500 pM, 600 pM, 700 pM, 800 pM, 900 pM, 1 nM, 1.1.nM, 1.2 nM, 1.3 nM, 1.4 nM, 1.5 nM, etc.) In some embodiments, binding is considered to be low affinity if the affinity is the same or lower (e.g., the Kd' is about the same or higher) for a polypeptide of interest than for a selected reference polypeptide. In some embodiments, binding is considered to be low affinity if the ratio of the Kd' for a polypeptide of interest to the Kd' for a selected reference polypeptide is 1:1 or more (e.g., 1.1:1, 1.2:1, 1.3:1, 1.4:1, 1.5:1. 1.6:1, 1.7:1, 1.8:1, 1.9:1, 2:1, 3:1, 4:1, 5:1, 10:1 or more). In some embodiments, binding is considered to be low affinity if the Kd' for a polypeptide of interest is 100% or more (e.g., 100%, 105%, 110%, 115%, 120%, 125%, 130%, 135%, 140%, 145%, 150%, 155%, 160%, 165%, 170%, 175%, 180%, 185%, 190%, 195%, 200%, 300%, 400%, 500%, 1000%, or more) of the Kd' for a selected reference polypeptide.

Mutant: As used herein, the term “mutant” refers to an entity that shows significant structural identity with a reference entity but differs structurally from the reference entity in the presence or level of one or more chemical moieties as compared with the reference entity. In many embodiments, a mutant also differs functionally from its reference entity. In general, whether a particular entity is properly considered to be a “mutant” of a reference entity is based on its degree of structural identity with the reference entity. As will be appreciated by those skilled in the art, any biological or chemical reference entity has certain characteristic structural elements. A mutant, by definition, is a distinct chemical entity that shares one or more such characteristic structural elements. To give but a few examples, a small molecule may have a characteristic core structural element (e.g., a macrocycle core) and/or one or more characteristic pendent moieties so that a mutant of the small molecule is one that shares the core structural element and the characteristic pendent moieties but differs in other pendent moieties and/or in types of bonds present (single vs double, E vs Z, etc) within the core, a polypeptide may have a characteristic sequence element comprised of a plurality of amino acids having designated positions relative to one another in linear or three-dimensional space and/or contributing to a particular biological function, a nucleic acid may have a characteristic sequence element comprised of a plurality of nucleotide residues having designated positions relative to on another in linear or three-dimensional space. For example, a mutant polypeptide may differ from a reference polypeptide as a result of one or more differences in amino acid sequence and/or one or more differences in chemical moieties (e.g., carbohydrates, lipids, etc) covalently attached to the polypeptide backbone. In some embodiments, a mutant polypeptide shows an overall sequence identity with a reference polypeptide that is at least 85%, 86%, 87%, 88%, 89%, 90%, 91%, 92%, 93%, 94%, 95%, 96%, 97%, or 99%. Alternatively or additionally, in some embodiments, a mutant polypeptide does not share at least one characteristic sequence element with a reference polypeptide. In some embodiments, the reference polypeptide has one or more biological activities. In some embodiments, a mutant polypeptide shares one or more of the biological activities of the reference polypeptide. In some embodiments, a mutant polypeptide lacks one or more of the biological activities of the reference polypeptide. In some embodiments, a mutant polypeptide shows a reduced level of one or more biological activities as compared with the reference polypeptide.

Non-natural amino acid: The phrase “non-natural amino acid” refers to an entity having the chemical structure of an amino acid (i.e.,: 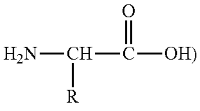 )

and therefore being capable of participating in at least two peptide bonds, but having an R group that differs from those found in nature. In some embodiments, non-natural amino acids may also have a second R group rather than a hydrogen, and/or may have one or more other substitutions on the amino or carboxylic acid moieties.

Pandemic strain: A “pandemic” influenza strain is one that has caused or has capacity to cause pandemic infection of human populations. In some embodiments, a pandemic strain has caused pandemic infection. In some embodiments, such pandemic infection involves epidemic infection across multiple territories; in some embodiments, pandemic infection involves infection across territories that are separated from one another (e.g., by mountains, bodies of water, as part of distinct continents, etc) such that infections ordinarily do not pass between them.

Polypeptide: A “polypeptide”, generally speaking, is a string of at least two amino acids attached to one another by a peptide bond. In some embodiments, a polypeptide may include at least 3-5 amino acids, each of which is attached to others by way of at least one peptide bond. Those of ordinary skill in the art will appreciate that polypeptides sometimes include “non-natural” amino acids or other entities that nonetheless are capable of integrating into a polypeptide chain, optionally. In some embodiments, the term “polypeptide” is used to refer to specific functional classes of polypeptides, such as, HA polypeptides, etc. For each such class, the present specification provides and/or the art is aware of several examples of amino acid sequences of known exemplary polypeptides within the class; in some embodiments, one or more such known polypeptides is/are reference polypeptides for the class. In such embodiments, the term “polypeptide” refers to any member of the class that shows sufficient sequence homology or identity with a relevant reference polypeptide that one skilled in the art would appreciate that it should be included in the class. In many embodiments, such member also shares significant activity with the reference polypeptide. For example, in some embodiments, a member polypeptide shows an overall degree of sequence homology or identity with a reference polypeptide that is at least about 30-40%, and is often greater than about 50%, 60%, 70%, 80%, 90%, 91%, 92%, 93%, 94%, 95%, 96%, 97%, 98%, 99% or more and/or includes at least one region (i.e., a conserved region, often including a characteristic sequence element) that shows very high sequence identity, often greater than 90% or even 95%, 96%, 97%, 98%, or 99%. Such a conserved region usually encompasses at least 3-4 and often up to 20 or more amino acids; in some embodiments, a conserved region encompasses at least one stretch of at least 2, 3, 4, 5, 6, 7, 8, 9, 10, 11, 12, 13, 14, 15 or more contiguous amino acids.

Predominantly present: The term “predominantly present”, as used herein, refers to the presence of an entity (e.g., an amino acid residue) at a particular location across a population. For example, an amino acid may be predominantly present if, across a population of polypeptides, a particular amino acid is statistically present in at least about 50%, about 55%, about 60%, about 65%, about 70%, about 75%, about 80%, about 85%, about 90%, about 95%, about 96%, about 97%, about 98%, about 99% or more of the polypeptides within a population of polypeptides.

Prevention: The term “prevention”, as used herein, refers to a delay of onset, and/or reduction in frequency and/or severity of one or more symptoms of a particular disease, disorder or condition (e.g., infection for example with influenza virus). In some embodiments, prevention is assessed on a population basis such that an agent is considered to “prevent” a particular disease, disorder or condition if a statistically significant decrease in the development, frequency, and/or intensity of one or more symptoms of the disease, disorder or condition is observed in a population susceptible to the disease, disorder, or condition.

Pure: As used herein, an agent or entity is "pure" if it is substantially free of other components. For example, a preparation that contains more than about 90% of a particular agent or entity is typically considered to be a pure preparation. In some embodiments, an agent or entity is at least 91%, at least 92%, at least 93%, at least 94%, at least 95%, at least 96%, at least 97%, at least 98%, or at least 99% pure.

Seeding potential: As used herein, the term "seeding potential" refers to a likelihood of an agent (e.g., an infectious agent such as a virus, a bacterium, etc.) to propagate infection. In some embodiments, seeding potential is correlated with the ability of an agent (e.g., an infectious agent such as a virus, a bacterium, etc.) to give rise to mutant progeny. For example, a seed strain may have 10%, 15%, 20%, 25%, 30%, 35%, 40%, 45%, 50%, 55%, 60%, 65%, 70%, 75%, 80%, 85%, 90%, 95%, or 100% mutant progeny.

Specificity: As is known in the art, "specificity" is a measure of the ability of a particular ligand (e.g., an antibody, an HA polypeptide, etc) to distinguish its binding partner (e.g., an antigen, a human HA receptor, and particularly a human upper respiratory tract HA receptor) from other potential binding partners (e.g., an avian HA receptor).

Substantially Similar: As used herein, the term "substantially similar" refers to a comparison between two entities. In general, entities are considered to be "substantially similar" to one another when they share sufficient structural similarity (e.g., a characteristic structural feature) that they have a comparable likelihood of sharing one or more additional attributes or features. To give but one example, a characteristic, for example, glycosylation site pattern, being either the same or similar enough between two influenza strains, that the human pandemic risk of each strain is the same.

Substantial sequence homology: The phrase "substantial homology" is used herein to refer to a comparison between amino acid or nucleic acid sequences. As will be appreciated by those of ordinary skill in the art, two sequences are generally considered to be "substantially homologous" if they contain homologous residues in corresponding positions. Homologous residues may be identical residues. Alternatively, homologous residues may be non-identical residues will appropriately similar structural and/or functional characteristics. For example, as is well known by those of ordinary skill in the art, certain amino acids are typically classified as "hydrophobic" or "hydrophilic" amino acids., and/or as having "polar" or "non-polar" side chains Substitution of one amino acid for another of the same type may often be considered a "homologous" substitution. Typical amino acid categorizations are summarized below:

| | | | | | |
|---|---|---|---|---|---|
| Alanine | Ala | A | Nonpolar | neutral | 1.8 |
| Arginine | Arg | R | Polar | positive | −4.5 |
| Asparagine | Asn | N | Polar | neutral | −3.5 |
| Aspartic acid | Asp | D | Polar | negative | −3.5 |
| Cysteine | Cys | C | Nonpolar | neutral | 2.5 |
| Glutamic acid | Glu | E | Polar | negative | −3.5 |
| Glutamine | Gln | Q | Polar | neutral | −3.5 |
| Glycine | Gly | G | Nonpolar | neutral | −0.4 |
| Histidine | His | H | Polar | positive | −3.2 |
| Isoleucine | Ile | I | Nonpolar | neutral | 4.5 |
| Leucine | Leu | L | Nonpolar | neutral | 3.8 |
| Lysine | Lys | K | Polar | positive | −3.9 |
| Methionine | Met | M | Nonpolar | neutral | 1.9 |
| Phenylalanine | Phe | F | Nonpolar | neutral | 2.8 |
| Proline | Pro | P | Nonpolar | neutral | −1.6 |
| Serine | Ser | S | Polar | neutral | −0.8 |
| Threonine | Thr | T | Polar | neutral | −0.7 |
| Tryptophan | Trp | W | Nonpolar | neutral | −0.9 |
| Tyrosine | Tyr | Y | Polar | neutral | −1.3 |
| Valine | Val | V | Nonpolar | neutral | 4.2 |

| Ambiguous Amino Acids | 3-Letter | 1-Letter |
|---|---|---|
| Asparagine or aspartic acid | Asx | B |
| Glutamine or glutamic acid | Glx | Z |
| Leucine or Isoleucine | Xle | J |
| Unspecified or unknown amino acid | Xaa | X |

As is well known in this art, amino acid or nucleic acid sequences may be compared using any of a variety of algorithms, including those available in commercial computer programs such as BLASTN for nucleotide sequences and BLASTP, gapped BLAST, and PSI-BLAST for amino acid sequences. Exemplary such programs are described in Altschul, et al., Basic local alignment search tool, *J. Mol. Biol.,* 215(3): 403-410, 1990; Altschul, et al., *Methods in Enzymology*; Altschul, et al., "Gapped BLAST and PSI-BLAST: a new generation of protein database search programs", *Nucleic Acids Res.* 25:3389-3402, 1997; Baxevanis, et al., *Bioinformatics: A Practical Guide to the Analysis of Genes and Proteins, Wiley,* 1998; and Misener, et al., (eds.), *Bioinformatics Methods and Protocols* (Methods in Molecular Biology, Vol. 132), Humana Press, 1999; all of the foregoing of which are incorporated herein by reference. In addition to identifying homologous sequences, the programs mentioned above typically provide an indication of the degree of homology. In some embodiments, two sequences are considered to be substantially homologous if at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or more of their corresponding residues are homologous over a relevant stretch of residues. In some embodiments, the relevant stretch is a complete sequence. In some embodiments, the relevant stretch is at least 10, at least 15, at least 20, at least 25, at least 30, at least 35, at least 40, at least 45, at least 50, at least 55, at least 60, at least 65, at least 70, at least 75, at least 80, at least 85, at least 90, at least 95, at least 100, at least 125, at least 150, at least 175, at least 200, at least 225, at least 250, at least 275, at least 300, at least 325, at least 350, at least 375, at least 400, at least 425, at least 450, at least 475, at least 500 or more residues.

Substantial sequence identity: The phrase "substantial identity" is used herein to refer to a comparison between amino acid or nucleic acid sequences. As will be appreciated by those of ordinary skill in the art, two sequences are generally considered to be "substantially identical" if they contain identical residues in corresponding positions. As is well known in this art, amino acid or nucleic acid sequences may be compared using any of a variety of algorithms, including those available in commercial computer programs such as BLASTN for nucleotide sequences and BLASTP, gapped BLAST, and PSI-BLAST for amino acid sequences. Exemplary such programs are described in Altschul, et al., Basic local alignment search tool, *J. Mol. Biol.,* 215(3): 403-410, 1990; Altschul, et al., *Methods in Enzymology*; Altschul, et al., "Gapped BLAST and PSI-BLAST: a new generation of protein database search programs", *Nucleic Acids Res.* 25:3389-3402, 1997; Baxevanis, et al., *Bioinfor-*

*matics: A Practical Guide to the Analysis of Genes and Proteins*, Wiley, 1998; and Misener, et al., (eds.), *Bioinformatics Methods and Protocols* (Methods in Molecular Biology, Vol. 132), Humana Press, 1999; all of the foregoing of which are incorporated herein by reference. In addition to identifying identical sequences, the programs mentioned above typically provide an indication of the degree of identity. In some embodiments, two sequences are considered to be substantially identical if at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or more of their corresponding residues are identical over a relevant stretch of residues. In some embodiments, the relevant stretch is a complete sequence. In some embodiments, the relevant stretch is at least 10, at least 15, at least 20, at least 25, at least 30, at least 35, at least 40, at least 45, at least 50, at least 55, at least 60, at least 65, at least 70, at least 75, at least 80, at least 85, at least 90, at least 95, at least 100, at least 125, at least 150, at least 175, at least 200, at least 225, at least 250, at least 275, at least 300, at least 325, at least 350, at least 375, at least 400, at least 425, at least 450, at least 475, at least 500 or more residues.

Substantial structural similarity: As used herein, the term "substantial structural similarity" refers to the presence of shared structural features such as presence and/or identity of particular amino acids at particular positions (see definitions of "shared sequence homology" and "shared sequence identity"). In some embodiments the term "substantial structural similarity" refers to presence and/or identity of structural elements (for example: loops, sheets, helices, H-bond donors, H-bond acceptors, glycosylation patterns, salt bridges, and disulfide bonds). In some other embodiments, the term "substantial structural similarity" refers to three dimensional arrangement and/or orientation of atoms or moieties relative to one another (for example: distance and/or angles between or among them between an agent of interest and a reference agent).

Therapeutic agent: As used herein, the phrase "therapeutic agent" refers to any agent that elicits a desired biological or pharmacological effect.

Treatment: As used herein, the term "treatment" refers to any method used to alleviate, delay onset, reduce severity or incidence, or yield prophylaxis of one or more symptoms or aspects of a disease, disorder, or condition. A treatment can be administered before, during, and/or after the onset of symptoms.

Unit dose: The expression "unit dose" as used herein refers to a physically discrete unit of a therapeutic/pharmaceutical composition, formulated for administration to a subject. In many embodiments, a unit dose contains a predetermined quantity of an active agent. In some embodiments, a unit dose contains an entire single dose of the agent. In some embodiments, more than one unit dose is administered to achieve a total single dose. In some embodiments, administration of multiple doses is required, or expected to be required, in order to achieve an intended effect. The unit dose may be, for example, a volume of liquid (e.g., an acceptable carrier) containing a predetermined quantity of one or more therapeutic agents, a predetermined amount of one or more therapeutic agents in solid form, a sustained release formulation or drug delivery device containing a predetermined amount of one or more therapeutic agents, etc. It will be appreciated that a unit dose may contain a variety of components in addition to the therapeutic agent(s). For example, acceptable carriers (e.g., pharmaceutically acceptable carriers), diluents, stabilizers, buffers, preservatives, etc., may be included as described infra. It will be understood, however, that the total daily usage of a formulation of the present disclosure will often be decided by the attending physician within the scope of sound medical judgment. In some embodiments, the specific effective dose level for any particular subject or organism may depend upon a variety of factors including the disorder being treated and the severity of the disorder; activity of specific active compound employed; specific composition employed; age, body weight, general health, sex and diet of the subject; time of administration, and rate of excretion of the specific active compound employed; duration of the treatment; drugs and/or additional therapies used in combination or coincidental with specific compound(s) employed, and like factors well known in the medical arts.

Vaccination: As used herein, the term "vaccination" refers to the administration of a composition intended to generate an immune response, for example to a disease-causing agent. Vaccination can be administered before, during, and/or after exposure to a disease-causing agent, and/or to the development of one or more symptoms, and in some embodiments, before, during, and/or shortly after exposure to the agent. In some embodiments, vaccination includes multiple administrations, appropriately spaced in time, of a vaccinating composition.

Variant: As used herein, the term "variant" is a relative term that describes the relationship between a particular polypeptide of interest and a "parent" or "reference" polypeptide to which its sequence is being compared. A polypeptide of interest is considered to be a "variant" of a parent or reference polypeptide if the polypeptide of interest has an amino acid sequence that is identical to that of the parent but for a small number of sequence alterations at particular positions. Typically, fewer than 20%, 15%, 10%, 9%, 8%, 7%, 6%, 5%, 4%, 3%, 2% of the residues in the variant are substituted as compared with the parent. In some embodiments, a variant has 10, 9, 8, 7, 6, 5, 4, 3, 2, or 1 substituted residue as compared with a parent. Often, a variant has a very small number (e.g., fewer than 5, 4, 3, 2, or 1) number of substituted functional residues (i.e., residues that participate in a particular biological activity). Furthermore, a variant typically has not more than 5, 4, 3, 2, or 1 additions or deletions, and often has no additions or deletions, as compared with the parent. Moreover, any additions or deletions are typically fewer than about 25, about 20, about 19, about 18, about 17, about 16, about 15, about 14, about 13, about 10, about 9, about 8, about 7, about 6, and commonly are fewer than about 5, about 4, about 3, or about 2 residues. In some embodiments, the parent or reference polypeptide is one found in nature. As will be understood by those of ordinary skill in the art, a plurality of variants of a particular polypeptide of interest may commonly be found in nature, particularly when the polypeptide of interest is an infectious agent polypeptide.

DETAILED DESCRIPTION OF CERTAIN EMBODIMENTS

The present invention provides, among other things, compositions and methods for use in the detection, treatment, and/or prevention of influenza transmission and/or infection. In some embodiments, the present invention provides vaccine compositions, diagnostic kits, methods of making vaccine compositions.

In some embodiments, the present invention provides engineered polypeptides whose amino acid sequence includes an element corresponding to a reference sequence element, which reference sequence element comprises residues 53-278 of a reference H3 HA that does not mediate significant human infectivity, wherein the polypeptide's sequence element shows at least 80% overall sequence identity with the reference sequence element but is not identical to the reference sequence element in that it includes at least one of:

vii. a first antigenic site feature comprising
  a. $Xaa_{122}$+$Xaa_{133}$+$Xaa_{137}$+$Xaa_{143}$+$Xaa_{144}$+$Xaa_{145}$+$Xaa_{146}$;

viii. a second antigenic site feature comprising
  a. $Xaa_{155}$+Ser186+$Xaa_{188}$+$Xaa_{189}$+$Xaa_{193}$;

ix. a third antigenic site feature comprising
  a. Asn53+$Xaa_{54}$+Asp275+$Xaa_{278}$;

x. a fourth antigenic site feature comprising
  a. Arg201+Ser205+$Xaa_{207}$+Arg208+Ile217+Arg220;

xi. a fifth antigenic site feature comprising
  a. $Xaa_{62}$+$Xaa_{78}$+$Xaa_{81}$+$Xaa_{83}$; and xii. at least one N-linked glycosylation feature at the amino acids corresponding to amino acids 81 and 165 of the reference H3HA, wherein the position of the amino acids of each feature correspond to the referenced position of the reference H3 HA, and wherein $Xaa_{122}$ is either Thr or Gln, Xaa 133 is either Asn or Asp, $Xaa_{137}$ is selected from the group Asn, Gly, and Tyr, $Xaa_{143}$ is either Pro or Ser, $Xaa_{144}$ is selected from the group Gly, Ala, and Val, $Xaa_{145}$ is selected from the group Ser, Asn, and Lys, $Xaa_{146}$ is either Gly or Ser, $Xaa_{155}$ is either Thr or His, $Xaa_{188}$ is either Asn or Asp, $Xaa_{189}$ is either Gln or Arg, $Xaa_{103}$ is either Ser or Asn, $Xaa_{54}$ is either Asn or Ser, $Xaa_{278}$ is either Ile or Asn, $Xaa_{207}$ is either Arg or Lys, $Xaa_{62}$ is selected from the group Ile, Arg, and Lys, $Xaa_{78}$ is either Val or Asp, $Xaa_{81}$ is either Asn or Asp, and $Xaa_{83}$ is either Thr or Lys.

In some embodiments, the polypeptide includes at least two features. In some embodiments, the polypeptide includes at least three features. In some embodiments, the polypeptide includes at least four features. In some embodiments, the polypeptide includes at least two features. In some embodiments, the polypeptide includes at least five features. In some embodiments, the polypeptide includes all six features.

In some embodiments, provided polypeptides are between 100 amino acids and 400 amino acids, inclusive. In some embodiments, provided polypeptides are between 200 amino acids and 300 amino acids, inclusive. In some embodiments, the present invention provides vaccine compositions including one or more engineered polypeptides as described herein and a pharmaceutically acceptable carrier.

The present invention also provides, in some embodiments, methods of providing a vaccine including providing at least one antigen comprising a polypeptide whose sequence includes an element corresponding to a reference sequence element, which reference sequence element comprises residues 53-278 of a reference H3 HA that does not mediate significant human infectivity, wherein the polypeptide's sequence element shows at least 80% overall sequence identity with the reference sequence element but is not identical to the reference sequence element in that it includes at least one of:

i. a first antigenic site feature comprising
  a. $Xaa_{122}$+$Xaa_{133}$+$Xaa_{137}$+$Xaa_{143}$+$Xaa_{144}$+$Xaa_{145}$+$Xaa_{146}$;

ii. a second antigenic site feature comprising
  a. $Xaa_{155}$+Ser186+$Xaa_{188}$+$Xaa_{189}$+$Xaa_{193}$;

iii. a third antigenic site feature comprising
  a. Asn53+$Xaa_{54}$+Asp275+$Xaa_{278}$;

iv. a fourth antigenic site feature comprising
  a. Arg201+Ser205+$Xaa_{207}$+Arg208+Ile217+Arg220;

v. a fifth antigenic site feature comprising
  a. $Xaa_{62}$+$Xaa_{78}$+$Xaa_{81}$+$Xaa_{83}$; and vi. at least one N-linked glycosylation feature at the amino acids corresponding to amino acids 81 and 165 of the reference H3HA, wherein the position of the amino acids of each feature correspond to the referenced position of the reference H3 HA, wherein the position of the amino acids of each feature correspond to the referenced position of the reference H3 HA, and wherein $Xaa_{122}$ is either Thr or Gln, $Xaa_{133}$ is either Asn or Asp, $Xaa_{137}$ is selected from the group Asn, Gly, and Tyr, $Xaa_{143}$ is either Pro or Ser, $Xaa_{144}$ is selected from the group Gly, Ala, and Val, $Xaa_{145}$ is selected from the group Ser, Asn, and Lys, $Xaa_{146}$ is either Gly or Ser, $Xaa_{155}$ is either Thr or His, $Xaa_{188}$ is either Asn or Asp, $Xaa_{189}$ is either Gln or Arg, $Xaa_{193}$ is either Ser or Asn, $Xaa_{54}$ is either Asn or Ser, $Xaa_{278}$ is either Ile or Asn, $Xaa_{207}$ is either Arg or Lys, $Xaa_{62}$ is selected from the group Ile, Arg, and Lys, $Xaa_{78}$ is either Val or Asp, $Xaa_{81}$ is either Asn or Asp, and $Xaa_{83}$ is either Thr or Lys, and formulating the provided at least one antigen into a vaccine composition.

Influenza Infection

Influenza has a long history of pandemics, epidemics, resurgences and outbreaks. Avian influenza, including the H5N1 strain, is a highly contagious and potentially fatal pathogen, but it currently has only a limited ability to infect humans.

Influenza viruses are RNA viruses which are characterized by a lipid membrane envelope containing two glycoproteins, hemagglutinin (HA) and neuraminidase (NA), embedded in the membrane of the virus particle. The viral genome is made up of several negative sense single stranded RNA molecules. Several proteins are encoded by the viral genome. Neuraminidase (NA) is a viral surface glycoprotein that cleaves terminal sialic acid residues from carbohydrate moieties on the surfaces of infected cells, promoting the release of progeny viruses. Hemagglutinin (HA) is one of the major viral surface glycoproteins and involved in the binding of the virus to sialic acids on the surface of susceptible cells (Uiprasertkul et al. *Emerg. Infect. Dis.* 11:1036, 2005).

Influenza HA is a trimer of virus particles. Influenza HA is synthesized as HA0 by virus post-infection in cells that is cleaved by cellular proteases at the basic cleavage site into HA1 and HA2 mature forms, which is required for proper function of this surface protein and for viral life cycle. The M2 protein is an ion channel protein. The HA, NA, and M2 protein are present in the viral envelope which is derived from the host cell plasma membrane. A ribonucleoprotein complex comprises an RNA segment associated with nucleoprotein (NP) and three polymerases, PA, PB1, and PB2. The M1 protein is associated with both ribonucleoprotien and the envelope.

Annual epidemics of influenza occur when the antigenic properties of the viral HA and NA proteins are altered. The mechanism of altered antigenicity is twofold: antigenic shift, caused by genetic rearrangement between human and animal viruses after double infection of host cells, which can cause a pandemic; and antigenic drift, caused by small changes in the HA and NA proteins on the virus surface, which can cause influenza epidemics.

There are 16 known HA subtypes and 9 NA subtypes, and different influenza strains are named based on the number of the strain's HA and NA subtypes. Based on comparisons of amino acid sequence identity and of crystal structures, the HA subtypes have been divided into two main groups and four smaller clades. The different HA subtypes do not necessarily share strong amino acid sequence identity, but the overall 3D structures of the different HA subtypes are similar to one another, with several subtle differences that can be used for classification purposes. For example, the particular orientation of the membrane-distal subdomains in relation to a central α-helix is one structural characteristic commonly used to determine HA subtype (Russell et al., 2004 *Virology,* 325:287, 2004; incorporated herein by reference). Those skilled in the art are well familiar with sequence and other structural similarities and differences that can be used to define and/or to distinguish different subtypes and/or clades of influenza viruses.

Only three (H1, H2, and H3) of the sixteen HA subtypes have thus far become adapted for human infection. One reported characteristic of HAs that have adapted to infect humans (e.g., of HAs from the pandemic H1N1 (1918) and H3N2 (1967-68) influenza subtypes) is their ability to preferentially bind to α2-6 sialylated glycans in comparison with their avian progenitors that preferentially bind to α2-3 sialylated glycans (Skehel & Wiley, 2000 *Annu Rev Biochem,* 69:531; Rogers, & Paulson, 1983 *Virology,* 127:361; Rogers et al., 1983 *Nature,* 304:76; Sauter et al., 1992 *Biochemistry,* 31:9609; Connor et al., 1994 *Virology,* 205: 17; Tumpey et al., 2005 *Science,* 310:77; all of which are incorporated herein by reference).

Several crystal structures of HAs from H1 (human and swine), H2 (human and avian), H3 (avian) and H5 (avian) subtypes bound to sialylated oligosaccharides (of both α2-3 and α2-6 linkages) are available and provide molecular insights into the specific amino acids that are involved in distinct interactions of the HAs with these glycans (Eisen et al., 1997 *Virology,* 232:19; Ha et al., 2001 *Proc Natl Acad Sci USA,* 98:11181; Ha et al., 2003 *Virology,* 309:209; Gamblin et al., 2004 *Science,* 303:1838; Stevens et al., 2004 *Science,* 303:1866; Russell et al., 2006 *Glycoconj J* 23:85; Stevens et al., 2006 *Science,* 312:404; Xu R et al., 2010 *J Virol* 84(4):1715; Liu J, et al., 2009 *Proc Natl Acad Sci USA* 106(40):17175, all of which are incorporated herein by reference).

Influenza infection is mediated by interaction of HA with the surface of cells through binding to a glycoprotein receptor. Binding of HA to HA receptors is predominantly mediated by N-linked glycans on the HA receptors. Specifically, HA on the surface of flu virus particles recognizes sialylated glycans that are associated with HA receptors on the surface of the cellular host. After recognition and binding, the host cell engulfs the viral cell and the virus is able to replicate and produce many more virus particles to be distributed to neighboring cells. Some crystal structures of exemplary HA-glycan interactions have been identified and are presented in Table 1:

TABLE 1

Crystal Structures of HA-Glycan Complexes

| Abbreviation (PDB ID) | Virus Strain | Glycan (with assigned coordinates) |
|---|---|---|
| ASI30_H1_23 (1RV0) | A/Swine/Iowa/30 (H1N1) | Neu5Ac |
| ASI30_H1_26 (1RVT) | A/Swine/Iowa/30 (H1N1) | Neu5Acα6Galβ4GlcNAcβ3Galβ4Glc |
| APR34_H1_23 (1RVX) | A/Puerto Rico/8/34 (H1N1) | Neu5Acα3Galβ4GlcNAc |
| APR34_H1_26 (1RVZ) | A/Puerto Rico/8/34 (H1N1) | Neu5Acα6Galβ4GlcNAc |
| ADU63_H3_23 (1MQM) | A/Duck/Ukraine/1/63 (H3N8) | Neu5Acα3Gal |
| ADU63_H3_26 (1MQN) | A/Duck/Ukraine/1/63 (H3N8) | Neu5Acα6Gal |
| AAI68_H3_23 (1HGG) | A/Aichi/2/68 (H3N2) | Neu5Acα3Galβ4Glc |
| ADS97_H5_23 (1JSN) | A/Duck/Singapore/3/97 (H5N3) | Neu5Acα3Galβ3GlcNAc |
| ADS97_H5_26(1JSO) | A/Duck/Singapore/3/97 (H5N3) | Neu5Ac |
| Viet04_H5 (2FK0) | A/Vietnam/1203/2004 (H5N1) | |

HA - α2-6 sialylated glycan complexes were generated by superimposition of the CA trace of the HA1 subunit of ADU63_H3 and ADS97_H5 and Viet04_H5 on ASI30_H1_26 and APR34_H1_26 (H1). Although the structural complexes of the human A/Aichi/2/68 (H3N2) with α2-6 sialylated glycans are published (Eisen et al., 1997, *Virology,* 232: 19), their coordinates were not available in the Protein Data Bank. The SARF2 program was used to obtain the structural alignment of the different HA1 subunits for superimposition.

HA receptors are modified by either α2-3 or α2-6 sialylated glycans near the receptor's HA-binding site, and the type of linkage of the receptor-bound glycan can affect the conformation of the receptor's HA-binding site, thus affecting the receptor's specificity for different HAs.

For example, the glycan binding pocket of avian HA is narrow. According to the present invention, this pocket binds to the trans conformation of α2-3 sialylated glycans, and/or to cone-topology glycans, whether α2-3 or α2-6 linked.

HA receptors in avian tissues, and also in human deep lung and gastrointestinal (GI) tract tissues are characterized by α2-3 sialylated glycan linkages, and furthermore (according to the present invention), are characterized by glycans, including α2-3 sialylated and/or α2-6 sialylated glycans, which predominantly adopt cone topologies. HA receptors having such cone-topology glycans may be referred to herein as CTHArs.

By contrast, human HA receptors in the bronchus and trachea of the upper respiratory tract are modified by glycans which predominantly adopt umbrella topologies, for example including many α2-6 sialylated glycans. Unlike the α2-3 motif, the α2-6 motif has an additional degree of conformational freedom due to the C6-05 bond (Russell et al., *Glycoconj J* 23:85, 2006). HAs that bind to such α2-6 sialylated glycans have a more open binding pocket to accommodate the diversity of structures arising from this conformational freedom. Moreover, as described in PCT Patent Application Nos. PCT/US09/30056 and PCT/US07/18160, HAs may need to bind to glycans (e.g., α2-6 sialylated glycans) in an umbrella topology, and particularly may need to bind to such umbrella topology glycans with strong affinity and/or specificity, in order to effectively mediate infection of human upper respiratory tract tissues. HA receptors having umbrella-topology glycans may be referred to herein as UTHArs.

As a result of these spatially restricted glycosylation profiles, humans are not usually infected by viruses containing many wild type avian HAs (e.g., avian H3). Specifically, because the portions of the human respiratory tract that are most likely to encounter virus (i.e., the trachea and bronchi) lack receptors with cone glycans (e.g., α2-3 sialylated glycans, and/or short glycans) and wild type avian HAs typically bind primarily or exclusively to receptors associated with cone glycans (e.g., α2-3 sialylated glycans, and/or short glycans), humans rarely become infected with avian viruses. Only when in sufficiently close contact with virus that it can access the deep lung and/or gastrointestinal tract receptors having umbrella glycans (e.g., long α2-6 sialylated glycans) do humans become infected.

HA Polypeptides

The present invention defines and describes certain polypeptides, specifically including engineered HA polypeptides, that show overall sequence identity with a reference HA and also include particular structural features as described herein. The present invention also provides fragments of such HA polypeptides, including characteristic fragments (i.e., fragments whose amino acid sequence includes at least one characteristic sequence element). In some embodiments, provided HA polypeptides mediate significant human receptor binding and/or human infection and/or transmission (e.g., as assessed in an established or described assay system).

In some embodiments, provided polypeptides bind to umbrella topology glycans (e.g., long α2-6 sialylated glycans such as, for example, Neu5Acα2-6Galβ1-4GlcNAcβ1-3Galβ1-4GlcNAc-) with high affinity. For example, in some embodiments, provided polypeptides bind to umbrella topology glycans with an affinity comparable to that observed for a wild type HA that mediates infection of a humans (e.g., H1N1 HA or H3N2 HA). In some embodiments, provided polypeptides bind to umbrella glycans with an affinity that is at least 25%, 30%, 35%, 40%, 45%, 50%, 55%, 60%, 65%, 70%, 75%, 80%, 85%, 90%, 95%, 96%, 97%, 98%, 99%, or 100% of that observed under comparable conditions for a wild type HA that mediates infection of humans. In some embodiments, provided polypeptides bind to umbrella glycans with an affinity that is greater than that observed under comparable conditions for a wild type HA that mediates infection of humans.

In certain embodiments, binding affinity of provided polypeptides is assessed over a range of concentrations. Such a strategy provides significantly more information, particularly in multivalent binding assays, than do single-concentration analyses. In some embodiments, for example, binding affinities of provided polypeptides are assessed over concentrations ranging over at least 2, 3, 4, 5, 6, 7, 8, 9, 10 or more fold.

In certain embodiments, provided polypeptides show high affinity if they show a saturating signal in a multivalent glycan array binding assay such as those described herein. In some embodiments, provided polypeptides show high affinity if they show a signal above about 400000 or more (e.g., above about 500000, 600000, 700000, 800000, etc) in such studies. In some embodiments, binding agents as described herein show saturating binding to umbrella glycans over a concentration range of at least 2 fold, 3 fold, 4 fold, 5 fold or more, and in some embodiments over a concentration range as large as 10 fold or more.

Furthermore, in some embodiments, provided polypeptides bind to umbrella topology glycans (and/or to umbrella topology glycan mimics) more strongly than they bind to cone topology glycans. In some embodiments, provided polypeptides show a relative affinity for umbrella glycans vs cone glycans that is about 10, 9, 8, 7, 6, 5, 4, 3, or 2.

In some embodiments, provided polypeptides bind to α2-6 sialylated glycans; in some embodiments, provided polypeptides bind preferentially to α2-6 sialylated glycans. In certain embodiments, provided polypeptides bind to a plurality of different α2-6 sialylated glycans. In some embodiments, provided polypeptides are not able to bind to α2-3 sialylated glycans, and in other embodiments provided polypeptides are able to bind to α2-3 sialylated glycans.

In some embodiments, provided polypeptides bind to receptors found on human upper respiratory epithelial cells. In certain embodiments, provided polypeptides bind to HA receptors in the bronchus and/or trachea. In some embodiments, provided polypeptides are not able to bind receptors in the deep lung, and in other embodiments, provided polypeptides are able to bind receptors in the deep lung.

In some embodiments, provided polypeptides bind to at least about 10%, 15%, 20%, 25%, 30% 35%, 40%, 45%, 50%, 55%, 60%, 65%, 70%, 75%, 80%, 85%, 90% 95% or more of the glycans found on HA receptors in human upper respiratory tract tissues (e.g., epithelial cells).

In some embodiments, provided polypeptides are characterized in that they bind to a receptor binding site utilized by a pandemic strain of influenza, and in some embodiments compete with such pandemic strain (or a receptor-binding portion thereof), for binding to such site. In some embodiments, provided polypeptides are characterized by a high degree of antigenic identity to an HA polypeptide found in a pandemic influenza strain. In some embodiments, a high degree of antigenic identity is at least 70% (e.g. 75%, 80%, 85%, 90%, 95% or higher).

In some embodiments, provided polypeptides display an activity of interest (e.g., binding to umbrella-topology glycans, mediating human infectivity and/or transmissibility, etc) for example binding to umbrella-topology glycans as measured using the glycan array analysis described here where Kd' is in the range of sub-picomolar to 10 nanomolar and at a level relative to binding to cone-topology glycans of greater than 2 orders of magnitude, in some embodiments, such relative level is relative to a different activity of the same HA polypeptide (e.g., binding to cone-topology glycans, mediating non-human infectivity and/or transmissibility, etc). In some embodiments, such relative level is relative to the same activity of a different HA polypeptide (e.g., by a reference HA).

In some embodiments, provided polypeptides are variants of a parent or reference HA. In some such embodiments, provided polypeptides have amino acid sequences that shows an overall degree of identity, with but differ from that, of the parent or reference HA in the presence or absence of one or more of the features described herein. In some embodiments, provided polypeptides have amino acid sequences that differ from that of the parent or reference HA in the presence or absence of only one of the features described herein. In some embodiments, provided polypeptides have amino acid sequences that differ from that of the parent or reference HA in the presence or absence of 1, 2, 3, 4, or 5 of the features described herein. In some embodiments, provided variants are otherwise structurally identical to the parent or reference HA.

In some embodiments, the reference HA with which a provided polypeptide shows the specified degree of sequence identity is one that does not mediate significant human receptor binding and/or human infection and/or transmission; in some such embodiments, the provided polypeptide differs from the reference non-human-infecting HA both in the presence vs absence of one or more structural features as described herein and in ability to mediate significant human receptor binding and/or significant human infection and/or transmission. In some embodiments, the reference HA with which a provided polypeptide shows the specified degree of sequence identity does mediate significant human receptor binding and/or significant human infection and/or transmission; in some such embodiments, the provided polypeptide shares both one or more structural features as describe herein and one or more biological activities (e.g., ability to mediate significant human receptor binding and/or significant human infection and/or transmission) with the human-infecting reference HA.

Representative HAs that do not mediate significant human receptor binding and/or human infection and/or transmission (i.e., non-human-infecting HAs) include H5 HAs, for example, A/duck/Hunan/795/2002 (clade 2.1), A/Viet Nam/1194/2004 (clade 1), A/Indonesia/5/2005 (clade 2.1.3.2), A/bar-headed goose/Qinghai/1A/2005 (clade 2.2), A/Anhui/1/2005 (clade 2.3.4), A/goose/Guiyang/337/2006 (clade 4), A/Cambodia/R0405050/2007 (clade 1.1), A/common magpie/Hong Kong/5052/2007 (clade 2.3.2.1), A/chicken/Viet Nam/NCVD-016/2008 (clade 7.1), A/Egypt/N03072/2010 (clade 2.2.1), A/Hubei/1/2010 (clade 2.3.2.1)

Representative HAs that do mediate significant human receptor binding and/or human infection and/or transmission (i.e., human-infecting HAs) including, for example H3N2 strains including, but not limited to, A/Port Chalmers/1/1973 (H3N2), A/Scotland/840/74 (H3N2), A/Victoria/3/75 (H3N2), A/Texas/1/77(H3N2), A/Bangkok/01/1979(H3N2), A/Philippines/2/82(H3N2), A/Christchurch/4/1985(H3N2), A/Mississippi/1/85(H3N2), A/Leningrad/360/1986(H3N2), A/Shanghai/11/87(H3N2), A/Sichuan/02/87(H3N2), A/Beijing/353/89(H3N2), A/Guizhou/54/89(H3N2), A/Beijing/32/92(H3N2), A/Shangdong/9/93(H3N2), A/Johannesburg/33/94(H3N2), A/Wuhan/359/95(H3N2), A/Sydney/5/97 (H3N2), A/Moscow/10/99(H3N2), A/Fujian/411/2002 (H3N2), A/California/7/2004(H3N2), A/Wellington/1/2004 (H3N2), A/Brisbane/10/2007(H3N2), A/Perth/16/2009 (H3N2), and A/Victoria/361/2011(H3N2), H1N1 stains including, but not limited to, A/Chile/1/83(H1N1), A/Singapore/6/1986(H1N1), A/Bayern/7/95(H1N1), A/Beijing/262/95(H1N1), A/New Caledonia/20/1999(H1N1), A/Solomon Islands/3/2006(H1N1), A/Brisbane/59/2007(H1N1), and A/California/07/2009(H1N1), H2N2 strains including, but not limited to, A/Panama/1/66(H2N2), and A/Korea/426/1968(H2N2), and, in certain cases, H9N2 strains including, but not limited to A/guinea fowl/Hong Kong/WF10/99 (H9N2), A/wild duck/Nanchang/2-0480/2000(H9N2), A/turkey/Israel/689/2008(H9N2), A/chicken/Zhejiang/HE1/2009(H9N2), and A/chicken/Egypt/115617V/2011(H9N2).

In some embodiments, the present invention provides a novel framework to define amino acid mutations in the hemagglutinin (HA) of circulating avian influenza strains, that could result in a switch in binding preference to human glycan receptors and presentation of one or more antigenically novel HAs to a host. In some embodiments, the present invention provides a novel framework to analyze molecular features of antigenic sites of a candidate influenza HA in relation to its nearest human-adapted phylogenetic relative pandemic influenza HA. In some embodiments, the present invention demonstrates that currently circulating candidate influenza HAs have evolved such that their antigenic site features resemble those of pandemic influenza HAs and require fewer amino acid changes to switch receptor specificity. Application of such provided frameworks defines HA polypeptide variants having sequence features and activities as described herein.

In particular, the present invention describes six structural features that, when present in an H3 HA polypeptide as described herein, result in a significant level of one or more activities selected from the group consisting of human receptor binding, human infection and/or human transmission. In some embodiments, an activity is considered significant if it is observed at a level above a designated threshold. In some embodiments, an activity is considered significant if it is observed at a level relatively higher than a reference activity—such as the same activity in a comparable reference HA polypeptide, for example that lacks one or more particular sequence elements or features, or as a different activity by the same HA polypeptide (e.g., binding to a different target).

As described herein, the present invention defines at least six structural features that contribute to relevant activities of H3 HA polypeptides. In particular, in accordance with the present invention provided engineered HA polypeptides typically show at least 80%, 81%, 82%, 83%, 84%, 85%, 86%, 87%, 88%, 89%, 90%, 91%, 92%, 93%, 94%, 95%, 96%, 97%, 98%, 99% or greater overall sequence identity with a reference HA (e.g., with a reference H3 HA), but have a sequence that is not 100% identical to the reference HA in that the provided HA has an amino acid sequence that includes at least one of:

1) a first antigenic site feature comprising
   a. $Xaa_{122}+Xaa_{133}+Xaa_{137}+Xaa_{143}+Xaa_{144}+Xaa_{145}+Xaa_{146}$;
2) a second antigenic site feature comprising
   b. $Xaa_{155}+Ser186+Xaa_{188}+Xaa_{189}+Xaa_{193}$;
3) a third antigenic site feature comprising
   c. $Asn53+Xaa_{54}+Asp275+Xaa_{278}$;
4) a fourth antigenic site feature comprising
   d. $Arg201+Ser205+Xaa_{207}+Arg208+Ile217+Arg220$;
5) a fifth antigenic site feature comprising
   e. $Xaa_{62}+Xaa_{78}+Xaa_{81}+Xaa_{83}$; and
6) at least one N-linked glycosylation feature at the amino acids corresponding to amino acids 81 and 165 of the reference H3HA, wherein the position of the amino acids of each feature correspond to the referenced position of the reference H3 HA, and wherein $Xaa_{122}$ is either Thr or Gln, $Xaa_{133}$ is either Asn or Asp, $Xaa_{137}$ is selected from the group Asn, Gly, and Tyr, $Xaa_{143}$ is either Pro or Ser, $Xaa_{144}$ is selected from the group Gly, Ala, and Val, $Xaa_{145}$ is selected from the group Ser, Asn, and Lys, $Xaa_{146}$ is either Gly or Ser, $Xaa_{155}$ is either Thr or His, $Xaa_{188}$ is either Asn or Asp, $Xaa_{189}$ is either Gln or Arg, $Xaa_{103}$ is either Ser or Asn, $Xaa_{54}$ is either Asn or Ser, $Xaa_{278}$ is either Ile or Asn, $Xaa_{207}$ is either Arg or Lys, $Xaa_{62}$ is selected from the group Ile, Arg, and Lys, $Xaa_{78}$ is either Val or Asp, $Xaa_{81}$ is either Asn or Asp, and $Xaa_{83}$ is either Thr or Lys.

Nucleic Acids and Expression Systems

The present invention also provides nucleic acids that encode polypeptides described herein, including for example HA polypeptides, antibodies, etc, and/or fragments thereof. The present invention also provides nucleic acids that are complementary to and/or hybridize with such encoding nucleic acids.

In some embodiments, provided nucleic acids are single-stranded; in some embodiments they are double-stranded.

In some embodiments, provided nucleic acids have sequences and lengths, as will be appreciated by those skilled in the art, appropriate for their use as primers, probes, aptamers, siRNAs, antisense, etc). To give but a few examples, such nucleic acids can be used as primers in polymerase chain reaction (PCR), as probes for hybridization (including in situ hybridization), and/or as primers for reverse transcription-PCR (RT-PCR).

In certain embodiments, nucleic acids can be or comprise DNA and/or RNA. In some embodiments, inventive nucleic acids may include one or more non-natural nucleotides; in other embodiments, inventive nucleic acids include only natural nucleotides.

The present invention also provides expression systems, including in vitro systems, cell systems, and organisms that produce provided polypeptides, and/or fragments thereof.

In some embodiments, provided nucleic acids are at least 15 nucleotides in length. In some embodiments, provided nucleic acids are at least 20, 25, 30, 40, 50, 60, 70, 80, 90, 100, 500, or 1,000 nucleotides in length.

Detecting Agents

The present invention provides agents that detect (e.g., via direct or indirect binding) provided polypeptides, nucleic acids that encode them, cells or viruses that express or otherwise include them, etc.

In some embodiments, provided detecting agents bind, directly or indirectly, to their targets. In some embodiments, provided detecting agents bind specifically to their targets. In some embodiments, provided detecting agents distinguish between a provided polypeptide (or encoding nucleic acid, etc) and a comparable reference HA polypeptide (or encoding nucleic acid, etc). In some such embodiments, the detected target shows a predetermined degree, level, or type of structural similarity or identity with the reference entity. In some embodiments, the target differs from the reference with respect to one or more of the features described herein.

In some particular embodiments, provided detecting agents are antibodies (including fragments thereof) that bind to provided polypeptides. In some embodiments, such antibodies bind specifically to provided polypeptides. In some embodiments, provided antibodies discriminate between provided polypeptides and their cognate parent HAs. In some embodiments, provided antibodies discriminate between HA polypeptides and otherwise identical HAs that differ only in presence or absence of one or more of the features specifically set forth therein. In some embodiments, provided detecting agents are aptamers.

Antibodies

The present invention also provides, among other things, antibodies that bind to polypeptides, nucleic acids, cells, etc. In some embodiments, provided antibodies may be used for diagnostic purposes, for example, for detecting the presence or absence of a pandemic strain of influenza in a subject or population of subjects. In some embodiments, provided antibodies may be used to identify and/or characterize influenza viruses and/or infections.

Any of a variety of samples may be analyzed according to various embodiments including whole blood, plasma, saliva, sweat, urine, feces, and any other appropriate source of a sample. In some embodiments, provided diagnostic antibodies may be used as reagents in one or more diagnostic assays, such as a panel of assays for use in infectious disease screening. Exemplary assay formats include ELISA, immunofluorescence, and/or immunoblotting.

In some embodiments, antibodies that bind to provided polypeptides (or nucleic acids that encode them) do so in a manner that interferes with binding between such polypeptides and an HA receptor, such that levels of observed binding are reduced when the antibody is present as compared with when they are absent. In some embodiments, antibodies that bind to provided polypeptides do so in a manner that does not significantly interfere with binding between such polypeptides and an HA receptor.

Aptamers

In some embodiments, the present invention also provides aptamers that bind to provided HA polypeptides or nucleic acids that encode them. Identification and/or characterization of aptamers that bind (directly or indirectly and/or specifically) to provided polypeptides can be achieved through any of a variety of approaches, as will be appreciated by those of ordinary skill in the art.

For example, aptamers can be selected using the SELEX (Systematic Evolution of Ligands by Exponential Enrichment) method (Tuerk et al, *Science* 249:505, 1990). Typically, SELEX methodology involves providing a large (e.g., $10^{15}$ different molecules) library of nucleic acid molecules that is contacted with the target entity (e.g., a provided HA polypeptide or fragment thereof). The entity is contacted with members of the library for a time and under conditions sufficient to permit interaction (e.g., specific interaction) to occur.

Any of a variety of technologies is known in the art to physically isolate aptamers that interact with the target entity and/or to amplify them. In some embodiments, such isolated aptamers, which may represent a new library, enriched for members that bind to the target entity of interest, may be re-screened to further identify binding aptamers, for example that show a particular level of affinity and/or specificity.

Typically, after about 5-15 cycles of iterative selection, partitioning and amplification process, the library is reduced to a small number of aptamers that bind tightly to the target molecule. Individual aptamer molecules can be isolated, their nucleotide sequences determined, and their properties with respect to binding affinity and/or specificity measured and/or compared.

Isolated aptamers can then be refined, for example, to eliminate nucleotides that do not contribute to target binding and/or aptamer structure, thereby producing aptamers truncated to their core binding domain. See, for example, Jayasena, *Clin. Chem.* 45:1628, 1999 for review of aptamer technology; the entire teachings of which are incorporated herein by reference.

Competing Agents

The present invention provides systems for identifying and/or characterizing agents that compete with provided polypeptides for binding to HA receptors, and particularly to human HA receptors. Such agents may be useful, for example, in the treatment or prevention of infection mediated by an HA polypeptide having one or more structural features as described herein. In some embodiments, detecting agents as described above (including, for example, antibodies and/or aptamers) are also competing agents. In some embodiments, competing agents are not detecting agents and/or do not bind directly or indirectly to provided polypeptides.

Diagnostic and Surveillance Applications

The present invention provides a variety of methods and compositions useful in the detection, identification, and/or characterization of influenza viruses and/or infection. In particular embodiments, the invention provides compositions comprising detecting agents, which compositions can be contacted with clinical, pathological, or environmental samples in order to assess, for example, presence or level of a particular influenza strain, extent or progress of an influenza infection, etc.

In certain embodiments, the invention provides compositions and/or kits that specifically detect polypeptides as described herein with particular glycan binding and/or infectivity characteristics. Such compositions or kits may include detecting agents, for example such as antibodies that specifically recognize certain HA polypeptides (e.g., that bind to umbrella glycans and/or to α2-6 sialylated glycans and/or to long α2-6 sialylated glycans), which can be used to specifically detect such HA polypeptides, for example by ELISA, immunofluorescence, and/or immunoblotting.

Antibodies that bind to HA polypeptides can also be used in virus neutralization tests, in which a sample is treated with antibody specific to HA polypeptides of interest, and tested for its ability to infect cultured cells relative to untreated sample. If the virus in that sample contains such HA polypeptides, the antibody will neutralize the virus and prevent it from infecting the cultured cells. Alternatively or additionally, such antibodies can also be used in HA-inhibition tests, in which the HA protein is isolated from a given sample, treated with antibody specific to a particular HA polypeptide or set of HA polypeptides, and tested for its ability to agglutinate erythrocytes relative to untreated sample. If the virus in the sample contains such an HA polypeptide, the antibody will neutralize the activity of the HA polypeptide and prevent it from agglutinating erythrocytes (Harlow & Lane, Antibodies: A Laboratory Manual, CSHL Press, 1988; www.who.int/csr/resources/publications/influenza/WHO_CDS_CSR_NCS_2002_5/en/in dex.html; www.who.int/csr/disease/avian_influenza/guidelines/labtests/en/index.html). In other embodiments, such agents may include nucleic acids that specifically bind to nucleotides that encode particular HA polypeptides and that can be used to specifically detect such HA polypeptides by RT-PCR or in situ hybridization (www.who.int/csr/resources/publications/influenza/WHO_CDS_CSR_NCS_2002_5/en/i ndex.html; www.who.int/csr/disease/avian_influenza/guidelines/labtests/en/index.html). In certain embodiments, nucleic acids which have been isolated from a sample are amplified prior to detection. In certain embodiments, diagnostic reagents can be detectably labeled.

The present invention also provides kits containing reagents according to the invention for the generation of influenza viruses and vaccines. Contents of such kits include, but are not limited to, expression plasmids containing HA-encoding HA polypeptides of interest (nucleotides (or fragments, such as characteristic fragments). Alternatively or additionally, kits may contain expression plasmids that express HA polypeptides of interest (or characteristic or biologically active portions). Expression plasmids containing no virus genes may also be included so that users are capable of incorporating HA nucleotides from any influenza virus of interest. Mammalian cell lines may also be included with the kits, including but not limited to, Vero and MDCK cell lines. In certain embodiments, diagnostic reagents can be detectably labeled.

In certain embodiments, kits for use in accordance with the present invention may include: a reference sample, instructions for processing samples, performing the test, instructions for interpreting the results, buffers and/or other reagents necessary for performing the test. In certain embodiments the kit can comprise a panel of antibodies.

In some embodiments of the present invention, glycan arrays, as discussed above, may be utilized as diagnostics and/or kits.

In certain embodiments, inventive glycan arrays and/or kits are used to perform dose response studies to assess binding of HA polypeptides to umbrella glycans at multiple doses (e.g., as described herein). Such studies give particularly valuable insight into the binding characteristics of tested HA polypeptides, and are particularly useful to assess specific binding. Dose response binding studies of this type find many useful applications. To give but one example, they can be helpful in tracking the evolution of binding characteristics in a related series of HA polypeptide variants, whether the series is generated through natural evolution, intentional engineering, or a combination of the two.

In some embodiments, provided kits comprise instructions for use.

In certain embodiments, inventive glycan arrays and/or kits are used to induce, identify, and/or select binding agents (e.g., HA polypeptides, and/or HA polypeptide variants) having desired binding characteristics. For instance, in some embodiments, inventive glycan arrays and/or kits are used to exert evolutionary (e.g., screening and/or selection) pressure on a population of polypeptide binding agents (e.g., HA polypeptides).

Therapeutic Applications

In some embodiments, the present invention provides systems and technologies useful in the treatment or prevention of influenza treatment of influenza infection, prior to or after initiation of infection and/or development of one or more symptoms of infection.

For example, the present invention provides influenza infection treatment through administration of therapeutic compositions whose active component is or comprises appropriate provided HA polypeptides, nucleic acids, binding agents, etc, as described herein.

In some embodiments, such therapeutic compositions are administered to a subject suffering from or susceptible to an influenza infection. In some embodiments, a subject is considered to be suffering from an influenza infection in the subject is displaying one or more symptoms commonly associated with influenza infection. In some embodiments, the subject is known or believed to have been exposed to the influenza virus. In some embodiments, a subject is considered to be susceptible to an influenza infection if the subject is known or believed to have been exposed to the influenza virus. In some embodiments, a subject is known or believed to have been exposed to the influenza virus if the subject has been in contact with other individuals known or suspected to have been infected with the influenza virus and/or if the subject is or has been present in a location in which influenza infection is known or thought to be prevalent.

In some embodiments, subjects suffering from or susceptible to influenza infection are tested for antibodies to inventive binding agents prior to, during, or after administration of inventive therapeutic compositions. In some embodiments, subjects having such antibodies are not administered therapeutic compositions comprising inventive binding agents. In some embodiments, an appropriate dose of therapeutic composition and/or binding agent is selected based on detection (or lack thereof) of such antibodies.

In some embodiments, selection of a particular subject for treatment, particular binding agent or composition for administration, and/or particular dose or regimen for administration, is memorialized, for example in a written, printed, or electronic storage form.

Inventive therapeutic compositions may be administered prior to or after development of one or more symptoms of influenza infection.

In general, a therapeutic composition will include a therapeutic agent in addition to one or more inactive agents such as a sterile, biocompatible carrier including, but not limited to, sterile water, saline, buffered saline, or dextrose solution. Alternatively or additionally, the composition can contain any of a variety of additives, such as stabilizers, buffers, excipients (e.g., sugars, amino acids, etc), or preservatives.

Exemplary inactive agents include, for example, a sterile, biocompatible carrier including, but not limited to, sterile water, saline, buffered saline, or dextrose solution. Alternatively or additionally, any of a variety of solvents, dispersion media, diluents, or other liquid vehicles, dispersion or suspension aids, disintegrating agents, surface active agents, isotonic agents, thickening or emulsifying agents, preservatives, buffering agents, solid binders, granulating agents, lubricants, coloring agents, sweetening agents, flavoring agents, perfuming agents, and the like, may be utilized, as suited to the particular formulation or dosage form desired. Remington's *The Science and Practice of Pharmacy,* $21^{st}$ Edition, A. R. Gennaro, (Lippincott, Williams & Wilkins, Baltimore, Md., 2006; incorporated herein by reference) discloses various excipients used in formulating therapeutic compositions and known techniques for the preparation thereof. Except insofar as any conventional excipient medium is incompatible with a substance or its derivatives, such as by producing any undesirable biological effect or otherwise interacting in a deleterious manner with any other component of the pharmaceutical composition, its use is contemplated to be within the scope of this invention.

In some embodiments, a therapeutic composition will include a therapeutic agent that is encapsulated, trapped, or bound within a lipid vesicle, a bioavailable and/or biocompatible and/or biodegradable matrix, or other microparticle.

In some embodiments, provided compositions further comprise one or more adjuvants. Any adjuvant may be used in accordance with the present invention. A large number of adjuvants are known; a useful compendium of many such compounds is prepared by the National Institutes of Health and can be found on the internet (www.niaid.nih.gov/daids/vaccine/pdf/compendium.pdf). See also Allison (1998*, Dev. Biol. Stand.,* 92:3-11; incorporated herein by reference), Unkeless et al. (1998*, Annu. Rev. Immunol.,* 6:251-281; incorporated herein by reference), and Phillips et al. (1992*, Vaccine,* 10:151-158; incorporated herein by reference). Hundreds of different adjuvants are known in the art and could be employed in the practice of the present invention.

Therapeutic compositions may be administered using any amount and any route of administration effective for treatment and/or vaccination. The exact amount required will vary from subject to subject, depending on the species, age, and general condition of the subject, the severity of the infection, the particular composition, its mode of administration, its mode of activity, and the like. Therapeutic compositions are typically formulated in dosage unit form for ease of administration and uniformity of dosage. It will be understood, however, that the total daily usage of the compositions of the present invention will be decided by the attending physician within the scope of sound medical judgment. The specific therapeutically effective dose level for any particular subject or organism will depend upon a variety of factors including the disorder being treated and/or vaccinated and the severity of the disorder; the activity of the specific vaccine composition employed; the half-life of the composition after administration; the age, body weight, general health, sex, and diet of the subject; the time of administration, route of administration, and rate of excretion of the specific compound employed; the duration of the treatment; drugs used in combination or coincidental with the specific compound employed; and like factors, well known in the medical arts.

Therapeutic compositions of the present invention may be administered by any route. In some embodiments, therapeutic compositions of the present invention are administered by a variety of routes, including oral (PO), intravenous (IV), intramuscular (IM), intra-arterial, intramedullary, intrathecal, subcutaneous (SQ), intraventricular, transdermal, interdermal, intradermal, rectal (PR), vaginal, intraperitoneal (IP), intragastric (IG), topical (e.g., by powders, ointments, creams, gels, lotions, and/or drops), mucosal, intranasal, buccal, enteral, vitreal, sublingual; by intratracheal instillation, bronchial instillation, and/or inhalation; as an oral spray, nasal spray, and/or aerosol, and/or through a portal vein catheter.

At present the oral or nasal spray or aerosol route (e.g., by inhalation) is most commonly used to deliver therapeutic agents directly to the lungs and respiratory system. However, the invention encompasses the delivery of the inventive therapeutic composition by any appropriate route taking into consideration likely advances in the sciences of drug delivery.

In some embodiments, preparations for inhaled or aerosol delivery comprise a plurality of particles. In some embodiments, such preparations have a mean particle size of 4, 5, 6, 7, 8, 9, 10, 11, 12, or 13 microns. In some embodiments, preparations for inhaled or aerosol delivery are formulated as a dry powder. In some embodiments, preparations for inhaled or aerosol delivery are formulated as a wet powder, for example through inclusion of a wetting agent. in some embodiments, the wetting agent is selected from the group consisting of water, saline, or other liquid of physiological pH.

In some embodiments, inventive compositions are administered as drops to the nasal or buccal cavity. In some embodiments, a dose may comprise a plurality of drops (e.g., 1-100, 1-50, 1-20, 1-10, 1-5, etc.)

In some embodiments, inventive compositions are administered using a device that delivers a metered dosage of composition (e.g., of binding agent).

Suitable devices for use in delivering intradermal therapeutic compositions described herein include short needle devices such as those described in U.S. Pat. No. 4,886,499, U.S. Pat. No. 5,190,521, U.S. Pat. No. 5,328,483, U.S. Pat. No. 5,527,288, U.S. Pat. No. 4,270,537, U.S. Pat. No. 5,015,235, U.S. Pat. No. 5,141,496, U.S. Pat. No. 5,417,662. Intradermal compositions may also be administered by devices which limit the effective penetration length of a needle into the skin, such as those described in WO99/34850, incorporated herein by reference, and functional equivalents thereof. Also suitable are jet injection devices which deliver liquid vaccines to the dermis via a liquid jet injector or via a needle which pierces the stratum corneum and produces a jet which reaches the dermis. Jet injection devices are described for example in U.S. Pat. No. 5,480,381, U.S. Pat. No. 5,599,302, U.S. Pat. No. 5,334,144, U.S. Pat. No. 5,993,412, U.S. Pat. No. 5,649,912, U.S. Pat. No. 5,569,189, U.S. Pat. No. 5,704,911, U.S. Pat. No. 5,383,851, U.S. Pat. No. 5,893,397, U.S. Pat. No. 5,466,220, U.S. Pat. No. 5,339,163, U.S. Pat. No. 5,312,335, U.S. Pat. No. 5,503,627, U.S. Pat. No. 5,064,413, U.S. Pat. No. 5,520,639, U.S. Pat. No. 4,596,556, U.S. Pat. No. 4,790,824, U.S. Pat. No. 4,941,880, U.S. Pat. No. 4,940,460, WO 97/37705 and WO 97/13537. Also suitable are ballistic powder/particle delivery devices which use compressed gas to accelerate vaccine in powder form through the outer layers of the skin to the dermis. Additionally, conventional syringes may be used in the classical mantoux method of intradermal administration.

General considerations in the formulation and manufacture of therapeutic/pharmaceutical agents may be found, for example, in *Remington's Pharmaceutical Sciences,* $19^{th}$ ed., Mack Publishing Co., Easton, Pa., 1995.

Inventive therapeutic compositions may be administered in any dose appropriate to achieve a desired outcome. In some embodiments, the desired outcome is reduction in intensity, severity, and/or frequency, and/or delay of onset of one or more symptoms of infection (e.g., influenza infection).

In some embodiments, inventive therapeutic compositions are formulated to reduce immunogenicity of included agents. For example, in some embodiments, an included active agent is associated with (e.g., bound to) an agent, such as polyethylene glycol and/or carboxymethyl cellulose, that masks its immunogenicity. In some embodiments, an included active agent has additional glycosylation that reduces immunogenicity.

In some embodiments, the present invention provides kits for administration of inventive therapeutic compositions. For example, in some embodiments, the invention provides a kit comprising at least one dose of a binding agent. In some embodiments, the invention provides a kit comprising an initial unit dose and a subsequent unit dose of a binding agent. In some such embodiments, the initial unit dose is greater than the subsequent unit dose or wherein the two doses are equal.

In some embodiments, inventive kits (particularly those for administration of inventive compositions) comprise at least one component of a delivery device, e.g., an inhaler. In some such embodiments, the invention provides a kit comprising at least one component of a delivery device, e.g., an inhaler and a dose of an of a binding agent.

Vaccine Compositions

In some particular embodiments, the present invention provides therapeutic compositions that are vaccine compositions for use in preventing influenza infections, particularly when such infections are mediated by a human-adapted H3 HA. In some embodiments, such a vaccine composition comprises one or more provided HA polypeptides or fragments thereof, nucleic acids that encode them, expression systems that produce them, and/or competing agents that compete their interactions with one or more HA receptors. In some embodiments, such a vaccine composition comprises one or more adjuvants for promoting or stimulating an immune response in an individual to whom the vaccine composition is administered.

In some embodiments, the present invention provides for vaccines and the administration of these vaccines to a human subject. In certain embodiments, vaccines are compositions comprising one or more of the following: (1) inactivated virus, (2) live attenuated influenza virus, for example, replication-defective virus, (3) inventive polypeptides or fragments thereof, detecting agents, binding agents, nucleic acids, expression systems, cells or organisms as described herein.

In some embodiments, the present invention provides inactivated flu vaccines. In certain embodiments, inactivated flu vaccines comprise one of three types of antigen preparation: inactivated whole virus, sub-virions where purified virus particles are disrupted with detergents or other reagents to solubilize the lipid envelope ("split" vaccine) or purified HA polypeptide ("subunit" vaccine). In certain embodiments, virus can be inactivated by treatment with formaldehyde, beta-propiolactone, ether, ether with detergent (such as Tween-80), cetyl trimethyl ammonium bromide (CTAB) and Triton N101, sodium deoxycholate and tri(n-butyl) phosphate. Inactivation can occur after or prior to clarification of allantoic fluid (from virus produced in eggs); the virions are isolated and purified by centrifugation (Nicholson et al., eds., *Textbook of Influenza*, Blackwell Science, Malden, M A, 1998). To assess the potency of the vaccine, the single radial immunodiffusion (SRD) test can be used (Schild et al., *Bull. World Health Organ.,* 52:43-50 & 223-31, 1975; Mostow et al., *J. Clin. Microbiol.,* 2:531, 1975).

The present invention also provides live, attenuated flu vaccines, and methods for attenuation are well known in the art. In certain embodiments, attenuation is achieved through the use of reverse genetics, such as site-directed mutagenesis.

In some embodiments, influenza virus for use in vaccines is grown in eggs, for example, in embryonated hen eggs, in which case the harvested material is allantoic fluid. Alternatively or additionally, influenza virus may be derived from any method using tissue culture to grow the virus. Suitable cell substrates for growing the virus include, for example, dog kidney cells such as MDCK or cells from a clone of MDCK, MDCK-like cells, monkey kidney cells such as AGMK cells including Vero cells, cultured epithelial cells as continuous cell lines, 293T cells, BK-21 cells, CV-1 cells, or any other mammalian cell type suitable for the production of influenza virus (including upper airway epithelial cells) for vaccine purposes, readily available from commercial sources (e.g., ATCC, Rockville, Md.). Suitable cell substrates also include human cells such as MRC-5 cells. Suitable cell substrates are not limited to cell lines; for example primary cells such as chicken embryo fibroblasts are also included.

In some embodiments, inventive vaccines further comprise one or more adjuvants. For example, aluminum salts (Baylor et al., *Vaccine,* 20:S18, 2002) and monophosphoryl lipid A (MPL; Ribi et al., (1986, *Immunology and Immunopharmacology of bacterial endotoxins*, Plenum Publ. Corp., NY, p 407, 1986) can be used as adjuvants in human vaccines. Alternatively or additionally, new compounds are currently being tested as adjuvants in human vaccines, such as MF59 (Chiron Corp., www.chiron.com/investors/pressreleases/2005/051028.html), CPG 7909 (Cooper et al., *Vaccine,* 22:3136, 2004), and saponins, such as QS21 (Ghochikyan et al., *Vaccine,* 24:2275, 2006).

Additionally, some adjuvants are known in the art to enhance the immunogenicity of influenza vaccines, such as poly[di(carboxylatophenoxy)phosphazene] (PCCP; Payne et al., *Vaccine,* 16:92, 1998), interferon-γ (Cao et al., *Vaccine,* 10:238, 1992), block copolymer P1205 (CRL1005; Katz et al., *Vaccine,* 18:2177, 2000), interleukin-2 (IL-2; Mbwuike et al., *Vaccine,* 8:347, 1990), and polymethyl methacrylate (PMMA; Kreuter et al., *J. Pharm. Sci.,* 70:367, 1981).

In some embodiments, inventive vaccine compositions do not include adjuvants (e.g., provided compositions are essentially free of adjuvants). In some embodiments, inventive vaccine compositions do not include an alum adjuvant (e.g., provided compositions are essentially free of alum).

In some embodiments, vaccine compositions are formulated or otherwise designed or prepared for administration prior to symptoms, and/or to exposure. It will be appreciated by those skilled in the art, however, that in many embodiments vaccine compositions may alternatively or additionally be administered after exposure, infection, and/or development of symptoms.

Combination Therapy

Therapeutic compositions as described herein may be administered either alone or in combination with one or more other therapeutic agents including, but not limited to, vaccines and/or antibodies. By "in combination with," it is not intended to imply that the agents must be administered at the same time or formulated for delivery together, although these methods of delivery are within the scope of the invention. In general, each agent will be administered at a dose and on a time schedule determined for that agent. Additionally, the invention encompasses the delivery of inventive therapeutic compositions in combination with agents that may improve their bioavailability, reduce or modify their metabolism, inhibit their excretion, or modify their distribution within the body. Although the therapeutic compositions of the present invention can be used for treatment of any subject (e.g., any animal) in need thereof, they are most preferably used in the treatment of humans. In some embodiments, inventive therapeutic compositions are administered in combination with one or more of an anti-viral agent (e.g., Oseltamivir [tamiflu], Zanamavir [Releza], etc.) and/or a sialydase. In some embodiments, inventive therapeutic compositions are administered in a combination with one or more other therapies (e.g., pain relievers, decongestants, cough suppressants, sleep aids, etc) commonly used to treat influenza infection or symptoms thereof.

Exemplary Uses

In some embodiments, the present invention provides technologies and methodologies for treating, monitoring and even predicting evolution of sequences of avian influenza HA strains.

Treatment of Influenza Infections

The present invention provides methods of treating influenza infection. In certain embodiments, such methods involve administering one or more inventive HA polypeptides or fragments thereof, nucleic acids that encode them, expression systems that produce them, and/or competing agents that compete their interactions with one or more HA receptors to a subject in need thereof. In some embodiments, HA polypeptides or fragments thereof, nucleic acids that encode them, expression systems that produce them, and/or competing agents that compete their interactions with one or more HA receptors inhibit the ability of HA (e.g. HA expressed on the surface of influenza virus) to bind to umbrella-topology glycans (e.g. glycans associated with human upper respiratory epithelial tissues, such as trachea and bronchus).

In some embodiments, HA polypeptides or fragments thereof, nucleic acids that encode them, expression systems that produce them, and/or competing agents that compete their interactions with one or more HA receptors of the present invention are used in the treatment of one or more of the following symptoms: fever, sore throat, muscle pains, severe headache, coughing, weakness, general discomfort, pneumonia, nausea, and/or vomiting. In certain embodiments, these symptoms are caused by influenza infection.

In some embodiments, inventive therapeutic compositions are administered to a subject suffering from or susceptible to an influenza infection. In some embodiments, a subject is considered to be suffering from an influenza infection in the subject is displaying one or more symptoms commonly associated with influenza infection. In some embodiments, the subject is known or believed to have been exposed to the influenza virus. In some embodiments, a subject is considered to be susceptible to an influenza infection if the subject is known or believed to have been exposed to the influenza virus. In some embodiments, a subject is known or believed to have been exposed to the influenza virus if the subject has been in contact with other individuals known or suspected to have been infected with the influenza virus and/or if the subject is or has been present in a location in which influenza infection is known or thought to be prevalent.

In some embodiments, the present invention provides a method of treating influenza infection comprising steps of (1) providing a patient exhibiting symptoms of influenza infection, and (2) administering a therapeutic amount of one or more HA polypeptides or fragments thereof, nucleic acids that encode them, expression systems that produce them, and/or competing agents that compete their interactions with one or more HA receptors to the patient. In some embodiments, the present invention provides a method of treating influenza infection comprising steps of (1) providing a patient suffering from influenza infection, and (2) administering a therapeutic amount of one or more HA polypeptides or fragments thereof, nucleic acids that encode them, expression systems that produce them, and/or competing agents that compete their interactions with one or more HA receptors to the patient. In some embodiments, the present invention provides a method of treating influenza infection comprising steps of (1) providing a patient susceptible to influenza infection, and (2) administering a therapeutic amount of one or more engineered HA polypeptides or fragments thereof, nucleic acids that encode them, expression systems that produce them, and/or competing agents that compete their interactions with one or more HA receptors to the patient.

In some embodiments, the present invention provides methods of treating influenza infection comprising steps of (1) providing a patient exhibiting symptoms of, suffering from, and/or susceptible to influenza infection, and (2) administering a substance that competes away the binding of HA polypeptides (e.g. HA polypeptides associated with influenza virus particles) with umbrella-topology glycans in human upper respiratory tissues.

In some embodiments, the present invention provides a method of preventing and/or delaying the onset of influenza infection comprising steps of (1) providing a patient susceptible to influenza infection, and (2) administering a therapeutic amount of one or more engineered HA polypeptides or fragments thereof, nucleic acids that encode them, expression systems that produce them, and/or competing agents that compete their interactions with one or more HA receptors to the patient.

Surveillance/Monitoring

Prior to the present invention, the effects of mutations in the immunodominant antigenic sites of H3 HA's had not been characterized. Presented herein, among other things, are methods for defining and understanding the requirements for an H3 HA to switch its binding preference to human receptors and present a pandemic risk. In some embodiments, a combination of amino acid substitutions and alteration of glycosylation pattern are combined to define mutations in the H3 HA that can result in greatly increased pandemic risk being presented by the H3 HA.

In some embodiments, the present invention provides methods of monitoring a population for human infective and/or human transmissible influenza. In some embodiments, methods of monitoring influenza in a sample include the steps of a) obtaining a sample from a source suspected to contain influenza, b) contacting the sample with one or more agents that specifically binds to a provided polypeptide, and c) detecting binding of the agent with the sample, so that presence and/or level of the H3 HA in the sample is determined. In some embodiments, the obtaining, contacting and detecting steps are repeated at least once after a period of time has elapsed since the first obtaining, contacting and detecting steps were completed.

In some embodiments, methods of determining pandemic risk from a strain of influenza are provided. In some embodiments, a method of monitoring influenza includes the steps of obtaining a sample from a source suspected to contain influenza, contacting the sample with one or more agents that specifically binds to an H3 HA polypeptide, detecting the binding of the agent with the sample, so that the presence and/or level of H3 HA in the sample is determined. In some embodiments, binding of the one or more agents to the sample indicates the presence of a human infective H3 HA. In some embodiments, binding of the one or more agents to the sample indicates the absence of a human infective H3 HA.

In some embodiment, methods according to the present invention may be used to analyze any of a variety of sample sources including environmental sources, human patient sources, or animal sources, for example. In some embodiments, analysis of one or more samples occurs at least twice. In some embodiments, each analysis is separated by a period of time to allow for longitudinal monitoring of a subject or population, for example. In some embodiments, the period of time may be: 1 hour, 12 hours, 1 day, 2 days, 3 days, 4 days, 5 days, 6 days, 1 week, 2 weeks, 3 weeks, 1 month, 2 months, 3 months, 4 months, 5 months, 6 months, or 1 year.

Detecting and/or Characterizing Useful Agents and/or Interactions

The present invention provides a variety of technologies for identification and/or characterization of useful agents (e.g., agents useful in the treatment, prevention, and/or analysis of influenza infection) and/or interactions.

For example, a variety of binding studies and/or formats are useful for the identification and/or characterization of useful agents as described herein. In some embodiments, the present invention utilizes systems for analyzing binding interactions between HA polypeptides and HA receptors. In some such embodiments, analysis methods comprise steps of 1) providing a source of HA polypeptides or binding components thereof; 2) providing a source of HA receptors or binding components thereof; and 3) contacting the provided sources with one another under conditions and for a time sufficient that binding between the HA polypeptides (or binding components thereof) and HA receptors (or binding components thereof) can be assessed. Such approaches can be utilized, for example, to identify or characterize HA polypeptides, in particular variant HA polypeptides, of interest, and/or to identify and/or characterize agents that bind thereto and/or inhibit interaction thereof with HA receptors.

In some embodiments, suitable sources of HA polypeptides or binding components thereof include, but are not limited to, pathological samples, such as blood, serum/plasma, peripheral blood mononuclear cells/peripheral blood lymphocytes (PBMC/PBL), sputum, urine, feces, throat swabs, dermal lesion swabs, cerebrospinal fluids, cervical smears, pus samples, food matrices, and tissues from various parts of the body such as brain, spleen, and liver. Alternatively or additionally, other suitable sources for samples containing HA polypeptides include, but are not limited to, environmental samples such as soil, water, and flora. Yet other samples include laboratory samples, for example of engineered HA polypeptides designed and/or prepared by researchers. Other samples that have not been listed may also be applicable. In some embodiments, sources (and/or samples contacted with HA receptors or binding components thereof) comprise intact virus or virus-like particles; in some embodiments, such sources and/or samples comprises HA polypeptides. In some embodiments, HA polypeptides are utilized in trimer form.

In some embodiments, suitable sources of HA receptors or binding components thereof include tissue samples; in some embodiments, suitable sources include isolated HA receptors or binding components thereof. In some embodiments, suitable sources include collections of glycans, for example in glycan arrays, comprising HA receptor glycans. In some embodiments, suitable sources include glycan collections comprising α2-3-linked and/or α2-6-linked glycans. In some embodiments, suitable sources include glycan collections comprising cone-topology and/or umbrella-topology glycans. In some embodiments, suitable sources include glycans found on human upper respiratory tract HA receptors.

It will be appreciated that a variety of binding interactions can usefully be studied in accordance with the present invention. In addition to HA polypeptide-HA receptor interactions, various antibody-antigen interaction or other ligand-target interactions may be studied, as described herein. For example, interactions between HA polypeptides and detecting or competing agents may be analyzed, in the presence or absence of HA receptors (or binding components thereof)

In some embodiments, one or both interacting components utilized in a binding study is detectably labeled (directly or indirectly) prior to, during, or after the contacting step. In some such embodiments, at least one interacting component is spatially localized, for example on an array. To give but one example, in some embodiments, a detectably labeled HA polypeptide or binding component thereof is contacted with a collection of glycans, for example on an array in which different glycans are distinctly localized. In some such embodiments, binding can be assessed by detecting and/or quantifying localized label (e.g., using a scanning device).

Alternatively or additionally, binding between or among interacting components or entities can be measured using, for example, calorimetric, fluorescence, or radioactive detection systems, or other labeling methods, or other methods that do not require labeling. In general, fluorescent detection typically involves utilizing a first interacting partner (e.g., an HA polypeptide or binding component thereof, or an HA receptor or binding portion thereof) that is or becomes labeled with a fluorescent molecule and monitoring fluorescent signals. Alternatively or additionally, one or both of the interacting components or entities can be tagged with a tag (e.g., biotin or streptavidin, antigen epitope, nucleic acid, etc) that itself interacts detectably with a partner (e.g., streptavidin or biotin, antibody, complementary nucleic acid).

In some embodiments, fluorescence quenching methods can be utilized in which one interacting component or entity is fluorescently labeled and the other is provided in a context that squelches the fluorescence if/when binding occurs.

Alternatively or additionally, binding studies can utilize live cells or tissue samples that have been grown in the presence of a radioactive substance, yielding a radioactively labeled probe. Binding in such embodiments can be detected by measuring radioactive emission.

Such methods are useful to determine the fact of binding and/or the extent of binding between interacting components or entities. In some embodiments, such methods can further be used to identify and/or characterize agents that interfere with or otherwise alter interactions of interest.

Methods described herein may be of particular use in, for example, identifying whether a molecule thought to be capable of interacting with a carbohydrate can actually do so, or to identify whether a molecule unexpectedly has the capability of interacting with a carbohydrate.

The present invention also provides methods of using glycan collections, for example, to detect a particular agent in a test sample. For instance, such methods may comprise steps of (1) contacting a collection of glycans (e.g., a glycan array) with a test sample (e.g., with a sample known or thought to contain an HA polypeptide); and, (2) detecting the binding of any agent in the test sample to the glycan collection.

Binding studies may be utilized in accordance with the present invention, for example, to determine kinetics of interaction between binding agent and glycan. For example, inventive methods for determining interaction kinetics may include steps of (1) contacting a glycan collection with a sample comprising the agent being tested, and, (2) measuring kinetics of interaction between the binding agent and the glycan(s).

The kinetics of interaction of between binding entities or components (e.g., a binding agent and glycans in a collection, for example on an array) can be measured by real time changes in, for example, colorimetric or fluorescent signals, as detailed above. Such methods may be of particular use in, for example, determining whether a particular binding agent is able to interact with a specific carbohydrate with a higher degree of binding than does a different binding agent interacting with the same carbohydrate.

In some embodiments, binding studies as described herein, and particularly binding studies that characterize interactions between HA polypeptides or binding components thereof and HA receptors or binding components thereof, are performed over a range of concentrations of one or both binding components or entities.

In some embodiments, binding (and/or infection and/or transmission) studies are performed in or utilizing an animal host. As used herein, an "animal host" includes any animal model suitable for influenza research. For example, animal hosts suitable for the invention can be any mammalian hosts, including primates, ferrets, cats, dogs, cows, horses, rodents such as, mice, hamsters, rabbits, and rats. In certain embodiments, an animal host used for the invention is a ferret. In particular, in some embodiments, an animal host is naïve to viral exposure or infection prior to administration of an inventive binding agent (optionally in an inventive composition). In some embodiments, the animal host is inoculated with, infected with, or otherwise exposed to virus prior to or concurrent with administration of an inventive binding agent. An animal host used in the practice of the present invention can be inoculated with, infected with, or otherwise exposed to virus by any method known in the art. In some embodiments, an animal host may be inoculated with, infected with, or exposed to virus intranasally.

In some embodiments, a suitable animal host may have a similar distribution of umbrella vs. cone topology glycans and/or $\alpha$2-6 glycans vs. a 2-3 glycans to the distribution found in the human respiratory tract. For example, it is contemplated that a ferret as an animal host may be more representative than a mouse when used as model of disease caused by influenza viruses in humans (Tumpey, et al. Science (2007) 315; 655-659). Without wishing to be bound any theories, the present invention encompasses the idea that ferrets may have a more similar distribution of glycans in the respiratory tract to those in the human respiratory tract than mouse does to human.

Naïve and/or inoculated animals may be used for any of a variety of studies. For example, such animal models may be used for virus transmission studies as in known in the art. It is contemplated that the use of ferrets in virus transmission studies may serve as a reliable predictor for virus transmission in humans. For example, air transmission of viral influenza from inoculated animals (e.g., ferrets) to naïve animals is known in the art (Tumpey, et al. Science (2007) 315; 655-659). Virus transmission studies may be used to test inventive binding agent polypeptides (e.g., HA polypeptides). For example, inventive binding agents may be administered to a suitable animal host before, during or after virus transmission studies in order to determine the efficacy of said binding agent in blocking virus binding and/or infectivity in the animal host. Using information gathered from virus transmission studies in an animal host, one may predict the efficacy of a binding agent in blocking virus binding and/or infectivity in a human host.

Production of Polypeptides

Provided polypeptides (e.g., HA polypeptides, antibodies, etc, and/or fragments, such as characteristic fragments, thereof) thereof, may be produced by any available means.

Polypeptides may be produced, for example, by utilizing a host cell system engineered to express nucleic acids encoding a polypeptide of interest. In some embodiments, such encoding nucleic acids are heterologous to the host cell system and are introduced into the system through action of the hand of man. Alternatively or additionally, the host cell system may be manipulated to express the encoding polypeptide at a particular (e.g., elevated) level and/or at a particular time.

Those skilled in the art will be aware of a wide variety of host cell systems that can appropriately be used to produce polypeptides as described herein. For example, polypeptides may be produced in microbial, mammalian, avian, or plant cell systems. In some embodiments, eukaryotic cell systems are utilized. In some embodiments, utilized cell systems are or comprise intact tissues and/or organisms. To give but a few examples, in some embodiments, provided polypeptides are expressed in egg, baculovirus, plant, yeast, Madin-Darby Canine Kidney cells (MDCK), or Vero (African green monkey kidney) cell systems.

Alternatively or additionally, provided polypeptides may be synthesized in vitro, for example utilizing in vitro transcription and/or translation systems and/or through chemical synthesis.

In some embodiments, provided HA polypeptides (or certain fragments thereof) may be produced in the context of intact virus or virus-like particles.

In some embodiments, provided HA polypeptides (or certain fragments thereof) can be isolated and/or purified from influenza virus. For example, virus may be grown in eggs, such as embryonated hen eggs, in which case the harvested material is typically allantoic fluid. Alternatively or additionally, virus may be grown in a tissue culture system. Suitable cell substrates for growing the virus include, for example, dog kidney cells such as MDCK or cells from a clone of MDCK, MDCK-like cells, monkey kidney cells such as AGMK cells including Vero cells, cultured epithelial cells as continuous cell lines, 293T cells, BK-21 cells, CV-1 cells, or any other mammalian cell type suitable for the production of influenza virus for vaccine purposes, readily available from commercial sources (e.g., ATCC, Rockville, Md.). Suitable cell substrates also include human cells such as MRC-5 cells. Suitable cell substrates are not limited to cell lines; for example primary cells such as chicken embryo fibroblasts are also included.

It will be appreciated by those of ordinary skill in the art that polypeptides, and particularly engineered HA polypeptides as described herein, may be generated, identified, isolated, and/or produced by culturing cells or organisms that produce the polypeptide (whether alone or as part of a complex, including as part of a virus particle or virus), under conditions that allow ready screening and/or selection of polypeptides that show desired binding and/or activity characteristics as described herein.

Samples

Those of ordinary skill in the art will appreciate that provided technologies can be applied to samples from any of a variety of sources including, for example, samples from systems, organisms, and/or environmental sources. Exemplary suitable sample sources include, but are not limited to, pathological samples, such as blood, serum/plasma, peripheral blood mononuclear cells/peripheral blood lymphocytes (PBMC/PBL), sputum, urine, feces, throat swabs, dermal lesion swabs, cerebrospinal fluids, cervical smears, pus samples, food matrices, and tissues from various parts of the body such as brain, spleen, and liver. Alternatively or additionally, other suitable sources for samples include, but are not limited to, environmental samples such as soil, water, and flora. Yet other samples include laboratory samples, for example of infectious disease polypeptides designed and/or prepared by researchers. Other samples that have not been listed may also be applicable.

EXEMPLIFICATION

Sequence evolution of Influenza HA

Influenza A virus poses a significant threat to global health both from the standpoint of seasonal outbreaks and also from that of the ability of avian viruses (antigenically novel to humans) to adapt to the human host. The sudden emergence of the antigenically novel 2009 H1N1 strain from multiple reassortment of influenza gene segments from avian, swine, and human viruses substantially impacted the global economy and highlighted the critical need for proper surveillance to be more prepared for such spontaneous pandemic outbreaks in the future. A characteristic property of human-adapted viruses such as H1N1, H2N2, and H3N2 is the quantitatively high binding affinity of the viral HA to human receptors in relation to its low to minimal binding to avian receptors.

Amino acid mutations in viral surface glycoprotein (HA) and polymerase (PB2) were able to confer aerosol transmission to avian H1N1 influenza isolate (Van Hoeven et al., 2009 *PNAS*, 106:3366). Among the avian subtypes known to infect humans, H5N1 has the highest mortality rate. It is therefore vital to implement new strategies for improved monitoring of the evolution of influenza viruses and to track their potential to adapt to the human host and potentially cause a pandemic.

The HA from avian subtypes typically binds to α2→3 sialylated glycans (or avian receptors)(Ge et al., 2011 *Crit Rev Microbiol.*, 37:157). A hallmark feature of human-adapted subtypes such as H1N1, H2N2, and H3N2 is the ability of their HA to bind preferentially to α2→6 sialylated glycan receptors (or human receptors). A switch in the quantitative binding preference to human receptors (high relative binding affinity to human receptor over avian receptor) has been shown to correlate with respiratory droplet transmissibility of the pandemic H1N1 and H2N2 viruses in ferrets (Tumpey et al., 2007 *Science*, 315:655; Srinivasan et al., 2008 *PNAS*, 105:2800; Pappas et al., 2010 *PLoS One*, 5:e11158; Viswanathan et al., 2010 *PLoS One*, 5:e13768).

Antigenic Identity (AI)

The AI metric is applied here to provide an analytical framework to human-adapted H1N1 and avian H2 subtypes for two reasons. First, to test the ability of AI values to discriminate the 1918 and 2009 pandemic HAs from seasonal strains. Second, to validate AI's potential to highlight the antigenic conservation of H2 in birds (Nabel G J, Wei C J, & Ledgerwood J E (2011) Vaccinate for the next H2N2 pandemic now. *Nature* 471(7337):157-158).

For H1N1, the human-adapted H1N1 strains were compared to 1918 pandemic H1N1 HA (A/South Carolina/1/18) and the characterized H1 antigenic sites Sa, Sb, Ca, Cb were used to calculate AI. The AI values clearly discriminate the reemerging swine-origin HA of 2009 H1N1 pandemic from the seasonal H1 based on its antigenic identity to the 1918 pandemic H1N1 HA (FIG. 1A). The reemerging swine-origin HA of the 2009 H1N1 pandemic and those that circulated during the 1918-40 period are characterized by AI values >70% and markedly differ from the strains that circulated during 1940-2008 (varies from 48% to 77% with an average of 55%). Two classical swine HA-carrying viruses, A/New Jersey/76 (H1N1) and A/Wisconsin/4754/1994 (H1N1), isolated between 1940-2008, also have high AI value and are genetically distinct when compared to the main cluster of human influenza viruses circulating in that period. Both strains are known to have caused human infections following pig-human interspecies transmission. The A/New Jersey/76 influenza virus is reported to have caused respiratory illness in 13 soldiers with 1 death at Fort Dix, N.J. (Gaydos J C, Top F H, Jr., Hodder R A, & Russell P K (2006) Swine influenza A outbreak, Fort Dix, N.J., 1976. *Emerg Infect Dis* 12(1):23-28 (in eng)). The A/Wisconsin/4754/1994 virus was recovered from a 39 year-old man who came in close contact with experimentally infected pigs (see Wentworth D E, McGregor M W, Macklin M D, Neumann V, & Hinshaw V S (1997) Transmission of swine influenza virus to humans after exposure to experimentally infected pigs. *J Infect Dis* 175(1):7-15).

For H2 subtype, the avian H2 strains were compared to the 1957-58 pandemic H2N2 HA (A/Albany/6/58(H2N2)) and the antigenic sites I-A, I-B, I-C, I-D, II-A and II-B characterized by hybridoma antibodies generated in BALB/c mice were used to calculate AI (see Tsuchiya E, et al. (2001) Antigenic structure of the haemagglutinin of human influenza A/H2N2 virus. *J Gen Virol* 82(Pt 10):2475-2484). Consistent with the findings of a previous report, the AI values indicate that the antigenic sites of the 1957-58 pandemic H2N2 HA are conserved in circulating avian H2 influenza (FIG. 1B). In fact, the antigenic sites of most avian H2 strains in circulation are 100% identical to the 1957-58 pandemic H2N2 HA (FIG. 1B). The conservation of antigenic sites in swine H2 influenza could not be assessed using this method due to lack of sequence information (H2N2 viruses do not circulate in swine, indeed, infection of swine with H2 viruses is rarely recorded). Similar to H1 subtype, the evolution of human H2 is characterized by steady antigenic drift leaning away from the pandemic strain. Although the majority of the strains that circulated during the immediate post-pandemic period 1957-68 have AI values >70%, HAs with AI ~60% started appearing after 1967 (FIG. 1B). It is reasonable to expect that the AI values would have decreased further had H2 continued to circulate in human population as a seasonal virus after 1968. These results indicate that viruses carrying pandemic HA-like genes can be distinguished from seasonal viruses using a cutoff value AI ~70%.

In the case of H3, the 5 antigenic sites (A-E) were used to calculate AI in reference to the prototypic pandemic strain of 1968 (A/Aichi/2/1968 (H3N2); see Wiley D C, Wilson I A, & Skehel J J (1981) Structural identification of the antibody-binding sites of Hong Kong influenza haemagglutinin and their involvement in antigenic variation. *Nature* 289(5796): 373-378; see also Wilson I A, Skehel J J, & Wiley D C (1981) Structure of the haemagglutinin membrane glycoprotein of influenza virus at 3 A resolution, *Nature* 289(5796): 366-373)). Unless stated otherwise henceforth an AI value for a given H3 HA sequence refers to its antigenic identity with the 1968 pandemic H3 HA.

Figure 4:
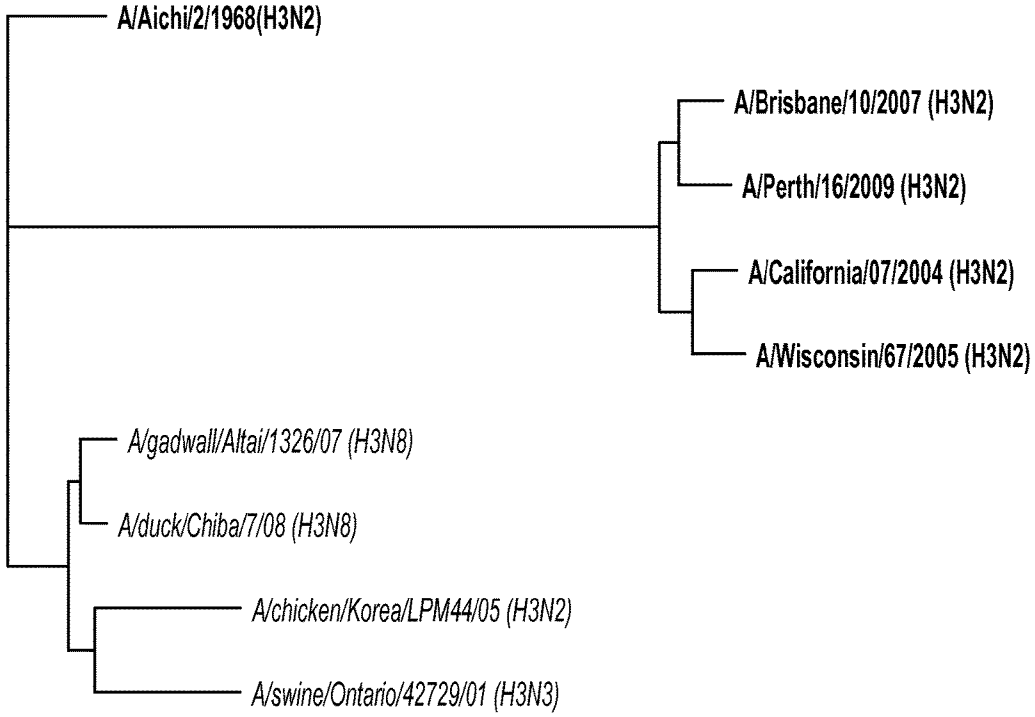
FIG. 4 depicts a phylogeny tree of 1968 pandemic HA and selected seasonal vaccine, avian and swine H3 HAs.

A total of 1,103 H3 avian and swine sequences were downloaded from the NCBI Influenza Database and analyzed. Of these 1,103 sequences, 756 were of avian origin and 347 were of swine origin. The avian sequences comprised nine different subtypes (H3N1-9), and the swine sequences comprised four different subtypes (H3N1, H3N2, H3N3 and H3N8). The avian and swine H3 amino acid sequences were compared against A/Aichi/2/1968 and AI values computed for each HA (FIG. 1C). In addition, a total of 3,632 human-adapted H3N2 strains were downloaded from the NCBI database and compared against 1968 pandemic H3 HA to enable a cross-species comparison of the antigenic drift (FIG. 1C). The AI values and phylogeny analysis indicated that, in comparison with human H3, avian and swine H3 are genetically and antigenically closer to the 1968 pandemic HA. Thus, we confirmed that avian and swine H3 are indeed antigenically intact (FIGS. 1C & 4).

In addition to the amino acids that constitute the antigenic sites, the attachment of complex glycans at specific glycosylation sites (Asn-X-Ser/Asn-X/Thr, where X is not a Proline) is also often part of the antigenic surface. An increase or decrease in the number of N-glycosylation sites therefore critically governs the antigenic properties of HA. The 1968 pandemic H3 HA carries only two glycosylation sites on the globular head region (at 81 & 165), whereas HA from seasonal strains carries an average of six sites (at 63, 122, 126, 133, 144, 165) (see Zhang M, et al. (2004) Tracking global patterns of N-linked glycosylation site variation in highly variable viral glycoproteins: HIV, SIV, and HCV envelopes and influenza hemagglutinin, *Glycobiology* 14(12):1229-1246). To incorporate glycosylation in the calculation of antigenic identity, the globular head region of the avian and swine HA sequences were examined for the conservation of 1968 pandemic H3-like glycosylation pattern. Among the 1,103 avian and swine H3 HA sequences, 359 carried additional glycosylation sites or positional shifts and therefore were removed from further consideration. The remaining 744 HA sequences (~67%) were found to possess the 1968 pandemic HA-like glycosylation pattern. Out of the 744 HA sequences, strains corresponding to 449 sequences (all avian) were isolated after 2000—many as recently as 2010—and their AI value exceed 70%. Extrapolating from H1 and H2 pandemic scenarios, these viruses are likely to pose a threat should they acquire the mutations necessary to crossover into human population.

Recently, the CDC reported the outbreak of a triple reassortant H3N2 from swine and released a set of sequences at Global Initiative on Sharing All Influenza Data (GISAID) following this event. The HA from a prototype outbreak strain, A/Minnesota/11/2010 (referred as Minn10), shares very high homology (approx. 98%) with a HA from swine A/swine/Minnesota/7931/2007(H3N2) (SwMinn10), and has good binding and transmission properties. Although the AI value of SwMinn10 (approx. 39%) is comparable to the recent seasonal HA, they share very low antigenic identity between them (only 15 out of the 27 [approx. 55%] antigenic positions are conserved). More importantly, the glycosylation pattern appears to be very different between SwMinn10 and seasonal HA. The SwMinn10 HA contains only three glycosylation sites in the globular head region, compared to 6 for the seasonal HA. The swine predecessor, SwMinn10, was not part of the 581 sequences identified by the analysis. This is due to its low AI value and the extra (third) glycosylation site in the head region. Although Minn10 cannot be regarded as a strain resembling the 1968 pandemic strain, this incident supports our theory that avian and swine strains that are divergent enough from the seasonal HA, both antigenically and with respect to their glycosylation pattern, need to be considered potential threats. Consequently, we relaxed the criteria used to identify potential pandemic strains and considered those HAs isolated after 2000, having matching glycosylation pattern as pandemic H3 and whose AI was equal to or greater than 49%, the maximum AI value of recent seasonal H3 (2000 or after) (FIG. 1C). This yielded 581 sequences (549 avian, 32 swine).

If any of the 581 sequences identified above should acquire the potential to crossover into humans, they would likely have a major impact on both immune recognition and vaccine efficacy. A previous study that examined H3N2 vaccine strain efficacy found that efficacy is inversely related to the fraction of amino acids that differ between the vaccine strain and a viral challenge strain in the dominant antigenic region (called $p_{epitope}$; see Gupta V, Earl D J, & Deem M W (2006), Quantifying influenza vaccine efficacy and antigenic distance, *Vaccine* 24(18): 3881-3888). The efficacy, defined in terms of the incidence of influenza-like illness in vaccinated individuals compared to unvaccinated individuals, was found to increase with decreasing values of $p_{epitope}$. The vaccine strain offers no cross-protection in cases where the $p_{epitope}$ exceeded 0.2 (~20%, expressed in percentage).

Figure 2:
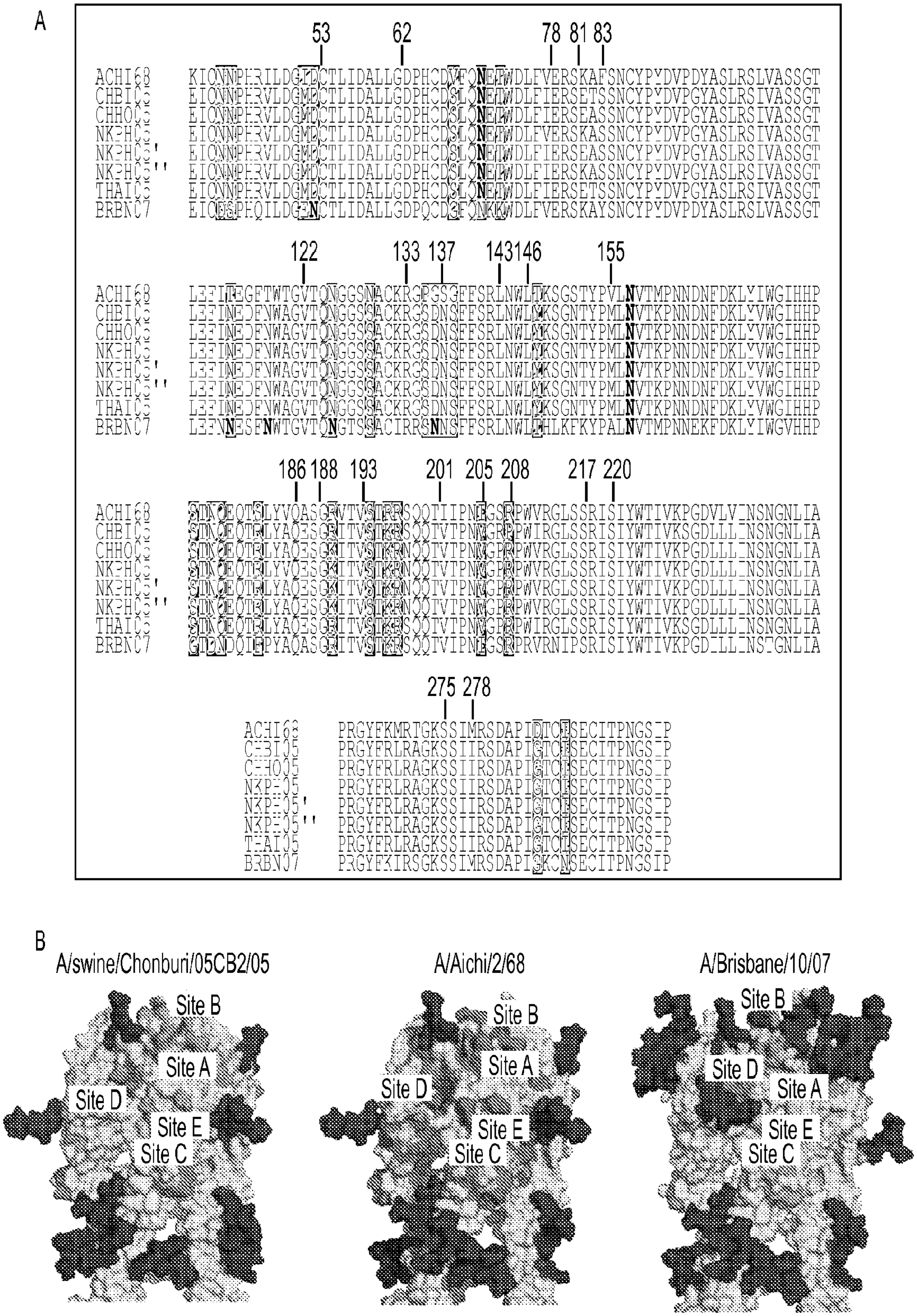
FIG. 2 illustrates genetic, antigenic and glycosylation pattern relatedness of the 1968 pandemic H3N2 HA to exemplary seasonal, swine and avian H3 HAs. A. shows a sequence alignment of the expanded globular head region (residues 50-328) of the HAs listed in Table 1. B. depicts surface rendered three-dimensional structural models of trimeric HA1 globular head regions of an exemplary pandemic (middle), seasonal (right), and swine (left) HAs.
Figure 3:
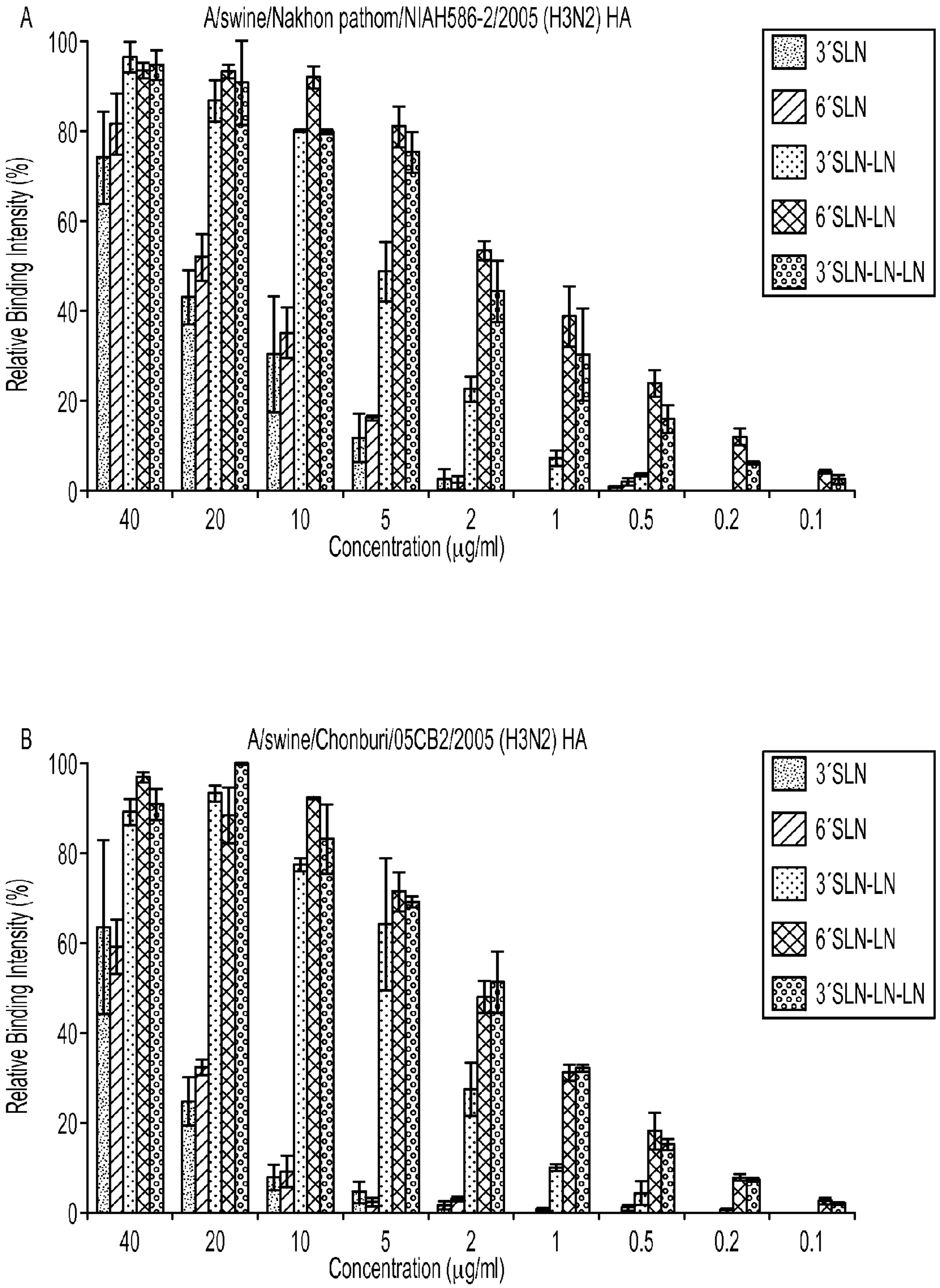
FIG. 3 shows binding profiles of exemplary H3 Has from indicated strains on a glycan binding array. A. A/swine/Nakhon pathom/NIAH586-2/2005, and B. A/swine/Chonburi/05CB2/2005. Both HAs show high affinity to representative avian and human glycan receptors as shown.

Currently, the H3N2 component of the annual influenza vaccine uses A/Perth/16/2009 (H3N2)-like virus. Based on the substitution pattern observed in recent years, antigenic site B of the H3N2 virus is believed to be the dominant epitope. The average $p_{epitope}$ value between avian/swine HA identified by the present study and A/Perth/16/2009-like (H3N2) HA is 0.78 (~78%). This suggests that the current vaccine strain is unlikely to offer cross-protection against the avian and swine HA if they crossover into humans. Importantly, out of the 581 HA sequences, six swine HAs already contain the prototypic mutations (L226, S228) necessary for HA human adaptation, and are thus capable of entering the human population either directly or via reassortment (Table 1, FIG. 2A). We recombinantly expressed HA derived from two swine isolates, A/swine/Chonburi/05CB2/2005 (H3N2) and A/swine/Nakhon pathom/NIAH586-2/2005 (H3N2), which have high AI value (Table 1) and characterized their relative binding affinities to representative avian and human receptors on a glycan array platform (FIG. 3).

Both swine HAs showed high affinity binding to both human and avian receptors. The high affinity human receptor-binding of these swine HAs appears to be in the same range as that of other seasonal H3 HAs characterized previously, and are thus capable of entering the human population either directly or via reassortment. The antigenic distance of these HAs (AI value and glycosylation pattern) to pandemic 1968 H3N2 strongly suggests that the six swine isolated viruses are of swine virus lineages and not examples of transient reverse zoonoses.

TABLE 1

Avian and swine HAs antigenically similar to the 1968 pandemic H3N2 HA

| Accession | Virus name | Abbreviation | AI % | Glycosylated positions |
|---|---|---|---|---|
| AAA43239 | A/Aichi/2/1968(H3N2) | ACHI68 | 100 | 81, 165 |
| ABY40417 | A/swine/Chonburi/05CB2/2005(H3N2) | CHBI05 | 56 | 81, 165 |
| ABY40412 | A/swine/Chachoengsao/NIAH586/2005 (H3N2) | CHHO05 | 52 | 81, 165 |
| ABY40414 | A/swine/Nakhon pathom/NIAH586-2/2005(H3N2) | NKPH05 | 52 | 81, 165 |
| BAH02120 | A/swine/Nakhon pathom/NIAH586-1/2005(H3N2) | NKPH05' | 52 | 81, 165 |
| ABY40413 | A/swine/Nakhon pathom/NIAH586-1/2005(H3N2) | NKPH05" | 52 | 81, 165 |
| ACM80372 | A/swine/Thailand/S1/2005(H3N2) | THAI05 | 56 | 81, 165 |
| ABW23353 | A/Brisbane/10/2007(H3N2) | BRBN07 | 37 | 63, 122, 126, 133, 144, 165 |
| ACS71642 | A/Perth/16/2009(H3N2) | PTH09 | 37 | 63, 122, 126, 133, 165 |

To understand the results from AI calculations in the context of the spatial relationship between glycosylation site and antigenic sites of H3 HA structural homology models of HA1 globular head of ACHI68, BRBN07 and CHIB05 HAs were constructed (see Table 1 for strain information). These structural models of HA comprised the basic trimannosyl core of N-linked glycan attached to the glycosylation sites (FIG. 2B). From the structural comparison it is clear that antigenic shape of HA which includes antigenic sites A-E and the glycosylation pattern of HA1 from the swine strain (CHIB05) closely resembles that of the 1968 pandemic HA. Conversely, the antigenic shape of a more recent seasonal strain (BRBN07) is remarkably different from that of the pandemic strain.

The H3 HA from some of the recent avian strains share approximately 86% overall sequence identity with the avian progenitor of the 1968 pandemic virus (A/duck/Ukraine/1/1963), reflecting antigenic intactness within birds. Many sequences from swine, some collected as recently as 2001, were also found to have high homology with the A/duck/Ukraine/1/1963 HA, indicating avian to swine transfer. For reasons that remain unclear, the more recent swine HAs (2006 and later) have diverged significantly from the 1968 pandemic virus (FIG. 1C) while the majority of swine H1 viruses remained antigenically stable from 1918 to the 1990s. Unlike the 1918 H1N1 virus which crossed to swine soon after and remained in swine, the human H3N2 viruses have repeatedly crossed from humans to swine for some time—quite possibly, this could be the reason why swine H3 viruses appear to manifest the antigenic drift that human strains underwent during this period. The frequent interspecies transmission of H3 viruses might also explain why this subtype is associated with the highest rates of mortality (see Thompson W W, et al. (2003), Mortality associated with influenza and respiratory syncytial virus in the United States, *JAMA* 289(2): 179-186).

Figure 5:
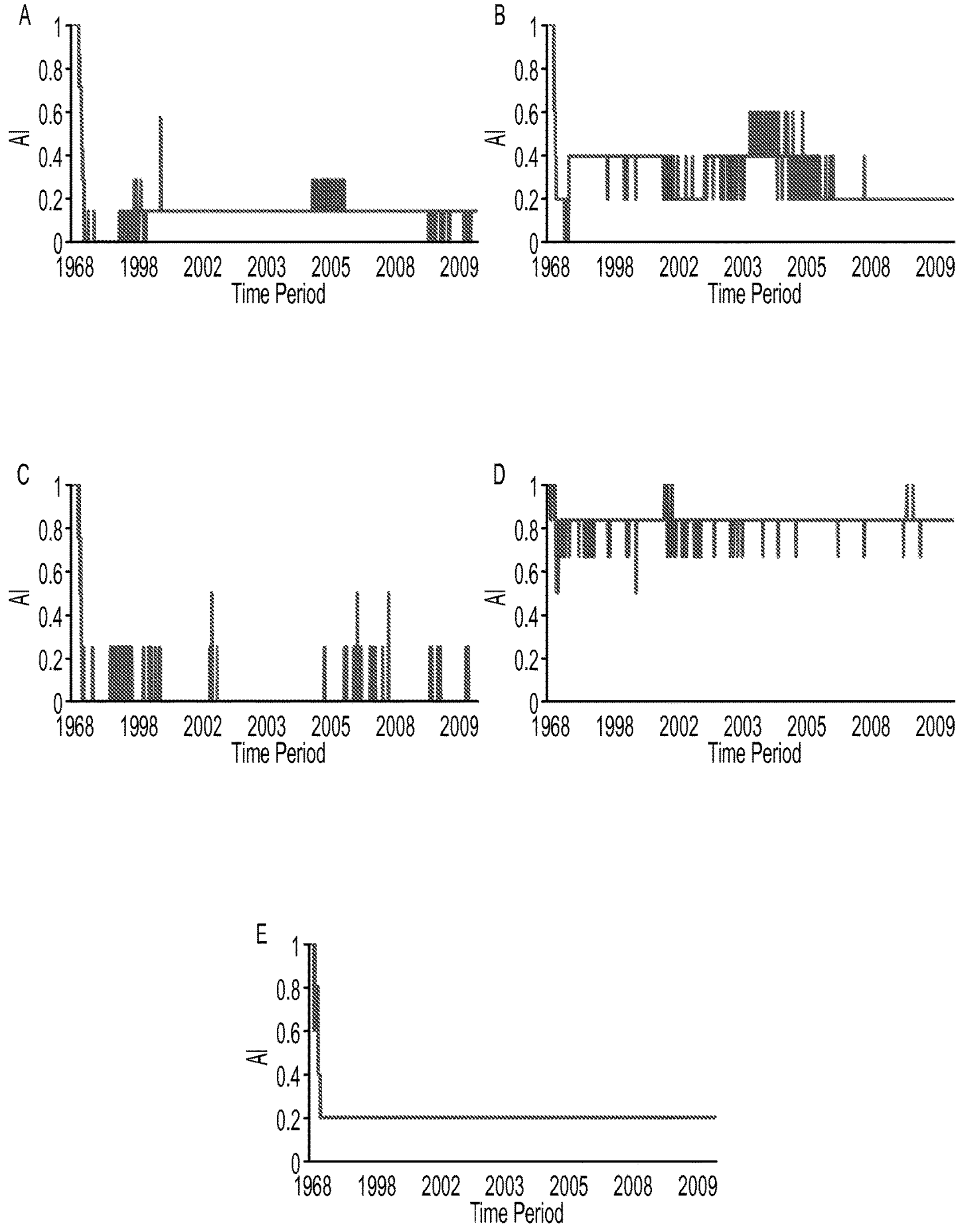
FIG. 5 shows N-linked glycosylation and antigenic drift of A/H3N2 HA across individual antigenic regions A-E before and after accumulation of glycosylation sites.

The importance of glycosylation in antigenic site masking leading to a new pandemic cycle and viral evolution became apparent after the 2009 pandemic. It was observed that the seasonal H1N1 HA carries antigenic site-masking glycosylation sites not present in the 2009 pandemic H1N1 HA (and 1918 H1N1 HA) and the exposure of the unprotected antigenic surface is believed to be the reason underpinning the severity of the 2009 H1N1 pandemic. Akin to H1 subtype, the additional glycosylation sites on the recent seasonal H3 appear to have a role in antigenic site-masking. For instance, the glycosylation at position 63 masks antigenic site E, and glycosylation at sites 122, 133, and 144 protect antigenic A. The shielding nature of these glycosylation sites is evident from the gradual decline in the mutation rate of the masked antigenic sites following their appearance (FIG. 5), portending a 2009 H1N1-like H3N2 pandemic.

If a strain carrying a HA similar to the ones identified by this analysis makes its way into humans, it would need to evolve rapidly in response to selective pressures from vaccination and herd immunity. The ability of H3 subtype to add glycosylation sites will be a key factor enabling the virus to achieve sustained circulation in the next cycle. In contrast, a previous study using nucleotide sequence analysis concluded that H2 has an intrinsically lower capacity to add glycosylation sites (see Igarashi M, Ito K, Kida H, & Takada A (2008), Genetically destined potentials for N-linked glycosylation of influenza virus hemagglutinin, *Virology* 376 (2): 323-329). Taking these factors together, we assert that it is less likely for an avian or swine H2 virus (antigenically similar to 1957-58 pandemic H2N2) to gain a foothold for sustained circulation in humans when compared to H3 viruses.

The rapid antigenic drift that human H3N2 HA underwent during the early adaptation period of the virus (1968-76) appears to have slowed down after 1977 (FIG. 1C). Interestingly, this time period also coincides with the reemergence of H1N1 in the human population. The (re-)emerging H1N1 subtype could have imposed strong selective pressures on the H3N2 to stop circulating in humans after 1977. The evolution of human H3N2 HA after 1977 is characterized by glycosylation accrual, low-level site-specific antigenic changes, and variations at other non-immunodominant sites (FIG. 1C). Based on this trend, one can argue that human H3N2 HA presently is "antigenically drained", which poses a substantially high barrier to evolution via antigenic drift. However, the presence of antigenically intact H3 in avian and swine suggests that, as with 2009 H1N1 pandemic, reassortment can result in 'resetting and shifting' the antigenicity back to that of the 1968 pandemic and hence facilitate sustained evolution of this subtype in humans.

The analyses presented in this Example portend a vaccine strategy to prevent a future H3 pandemic. Among the WHO recommended vaccine strains of influenza A/H3N2 virus, A/Hong Kong/1/1968(H3N2) will be effective ($p_{epitope}$<0.2) against 505 of 581 strains (~87%) identified by this study, and thus could be used for the development of pandemic influenza vaccine. Surprisingly, H3N2 vaccine strains that were subsequently used are not capable of being as effective. For instance, A/Port Chalmers/1/1973(H3N2), administered between 1974-76, can protect only against 69 strains (~12%). The discrepancy between the effectiveness of A/Hong Kong/1/1968(H3N2) and A/Port Chalmers/1/1973 (H3N2) is due to three mutations found in the antigenic site B of A/Port Chalmers/1/1973(H3N2) (at T155Y, N188D, S193N). These data suggest that a cocktail of A/Hong Kong/1/1968(H3N2) and an avian and swine strain each that represent the circulating influenza in birds and pigs can form the components of the pandemic influenza vaccine.

Although antigenic phenotypes could be predicted from HA sequences, the genetic signatures in influenza viruses that lead to a zoonosis cannot be accurately predicted. Although an antigenically novel HA is necessary, it is not the only determining factor for a pandemic. Importantly, while gain of host receptor specificity is a key determinant, changes in influenza proteins other than HA such as the polymerase (PB-2) are typically involved, making predictions of the timing of future pandemics more complex. We believe however, that close monitoring of viral evolution and inter-species transfers of swine and avian H3HA, followed by immunization against a cocktail of carefully selected H3 strains of current avian and swine origin along with specific past strains, could reduce the chances of future H3N2 pandemics (see Settembre E C, Dormitzer P R, & Rappuoli R (2010) H1N1: Can a pandemic cycle be broken?, *Sci Transl Med* 2(24): 24ps14).

Materials and Methods

Calculation of AI Values for H1, H2 and H3 Subtypes.

AI values were calculated using the characterized antigenic sites of H1, H2 and H3 HA. For H1, 128, 129, 158, 160, 162, 163, 165, 166, 167 (Sa); 156, 159, 192, 193, 196, 198 (Sb); 140, 143, 145, 169, 173, 182, 207, 224, 225, 240, 273 (Ca); 78, 79, 81, 82, 83, 122 (Cb) were used. For H2, 162, 248 (I-A); 137, 187 (I-B); 131, 222, 218 (I-C), 80, 200 (I-D); 40 (II-A), 273 (II-B) were used. For H3, 122, 133, 137, 143, 144, 145, 146 (A); 155, 186, 188, 189, 193 (B); 53, 54, 275, 278 (C); 201, 205, 207, 208, 217, 220 (D); 62, 78, 81, 83 (E) were used. Positions are numbered according to H3 molecule. The antigenic identity (AI) of an avian or a swine HA is defined by the percentage fraction of amino acids in the dominant antigenic sites that are conserved in the corresponding pandemic HA for each of the H1 (A/South Carolina/1/18), H2 (A/Albany/6/58(H2N2)) and H3 (A/Aichi/2/1968 (H3N2)) subtypes.

In Silico Identification of Glycosylation Sites— glycosylation sites are defined by the motif N-X-T/S, where X is any amino acid except Proline. A position in a HA amino acid sequence is considered to be glycosylated if it contains the N-X-T/S motif and is predicted by GlyProt (www.glycosciences.de/modeling/glyprot/php/main.php)—an online tool for in silico glycosylation of proteins.

Cloning, Baculovirus Synthesis, Recombinant Expression and Purification of Representative H3 HAs.

Soluble versions (lacking membrane proximal C-terminus region) of HA from representative H3N2 swine isolates A/swine/Chonburi/05CB2/2005 and A/swine/Nakhon pathom/NIAH586-2/2005 were recombinantly expressed (with C-terminal His-tag) as described previously (see Rinivasan A, et al. (2008) Quantitative biochemical rationale for differences in transmissibility of 1918 pandemic influenza A viruses, *Proc Natl Acad Sci USA* 105(8): 2800-2805). These representative H3 HAs had high AI values and the prototypic Leu226 and Ser228 residues characteristic of human-adapted H3 HAs. Briefly, recombinant baculoviruses with the HA gene were used to infect (MOI=1) suspension cultures of Sf9 cells (Invitrogen, Carlsbad, Calif.) cultured in BD Baculogold Max-XP SFM (BD Biosciences, San Jose, Calif.). The infection was monitored and the conditioned media was harvested 3-4 days post-infection. The soluble HA from the harvested conditioned media was purified using Nickel affinity chromatography (HisTrap HP columns, GE Healthcare, Piscataway, N.J.). Eluting fractions containing HA were pooled, concentrated and buffer exchanged into 1×PBS pH 8.0 (Gibco) using 100K MWCO spin columns (Millipore, Billerica, Mass.). The purified protein was quantified using BCA method (Pierce).

Glycan Array Analysis—

To investigate the multivalent HA-glycan interactions a streptavidin plate array comprising of representative biotinylated α2→3 and α2→6 sialylated glycans was used as described previously. 3'SLN, 3'SLN-LN, 3'SLN-LN-LN are representative avian receptors. 6'SLN and 6'SLN-LN are representative human receptors. The biotinylated glycans were obtained from the Consortium of Functional Glycomics through their resource request program. Streptavidin-coated High Binding Capacity 384-well plates (Pierce) were loaded to the full capacity of each well by incubating the well with 50 μl of 2.4 μM of biotinylated glycans overnight at 4° C. Excess glycans were removed through extensive washing with PBS. The trimeric HA unit comprises of three HA monomers (and hence three RBS, one for each monomer). The spatial arrangement of the biotinylated glycans in the wells of the streptavidin plate array favors binding to only one of the three HA monomers in the trimeric HA unit. Therefore in order to specifically enhance the multivalency in the HA-glycan interactions, the recombinant HA proteins were pre-complexed with the primary and secondary antibodies in the molar ratio of 421 (HA: primary: secondary). The identical arrangement of 4 trimeric HA units in the pre-complex for all the HAs permit comparison between their glycan binding affinities. A stock solution containing appropriate amounts of Histidine tagged HA protein, primary antibody (Mouse anti 6× His tag IgG) and secondary antibody (HRP conjugated goat anti Mouse IgG (Santacruz Biotechnology) in the ratio 4:2:1 and incubated on ice for 20 min. Appropriate amounts of pre-complexed stock HA were diluted to 250 μl with 1% BSA in PBS. 50 μl of this pre-complexed HA was added to each of the glycan-coated wells and incubated at room temperature for 2 hours followed by the above wash steps. The binding signal was determined based on HRP activity using Amplex Red Peroxidase Assay (Invitrogen, CA) according to the manufacturer's instructions. The experiments were done in triplicate. Minimal binding signals were observed in the negative controls including binding of pre-complexed unit to wells without glycans and binding of the antibodies alone to the wells with glycans.

EQUIVALENTS AND SCOPE

Those skilled in the art will recognize, or be able to ascertain using no more than routine experimentation, many equivalents to the specific embodiments of the invention described herein. The scope of the present invention is not intended to be limited to the above Description, but rather is as set forth in the following claims:

What is claimed is:

1. A vaccine composition comprising (i) engineered HA antigenic components; or (ii) antigens, in each case from a plurality of influenza strains, which plurality comprises:

A/Hong Kong/1/1968 (H3N2);

A circulating avian H3 influenza strain; and

A circulating swine H3 influenza strain.

2. A method of vaccinating a human population against influenza infection, the method comprising steps of:

administering the vaccine composition of claim 1 to members of a population upon detection of an H3 HA polypeptide showing at least 50% AI with A/Aichi/2/1968 (H3N2).

3. The method of claim 2, wherein the step of administering comprises administering to a subject when the detection is in a sample from the subject.

4. The method of claim 2, wherein the detection was in an environmental sample.

5. The composition of claim 1, wherein at least one of the engineered HA antigenic components is or comprises attenuated virus.

6. The composition of claim 1, wherein at least one of the engineered HA antigenic components is or comprises an isolated HA polypeptide.

* * * * *

UNITED STATES PATENT AND TRADEMARK OFFICE

CERTIFICATE OF CORRECTION

PATENT NO. : 10,301,359 B2
APPLICATION NO. : 14/888205
DATED : May 28, 2019
INVENTOR(S) : Sasisekharan et al.

It is certified that error appears in the above-identified patent and that said Letters Patent is hereby corrected as shown below:

In the Specification

In Column 1, Lines 9-12, delete:
“This invention was made with government support under Contract No. 6922267 awarded by the National Institutes of General Medical Sciences. The government has certain rights in the invention.”

And insert:
-- This invention was made with government support under GM057073 awarded by the National Institutes of Health. The government has certain rights in the invention. --

Signed and Sealed this
Fourth Day of November, 2025

John A. Squires
*Director of the United States Patent and Trademark Office*